US010627377B2

(12) United States Patent
Lewis et al.

(10) Patent No.: US 10,627,377 B2
(45) Date of Patent: Apr. 21, 2020

(54) ACCELERATED TESTING METHOD OF SILICONE DRAINAGE IN SYRINGES

(71) Applicant: Eli Lilly and Company, Indianapolis, IN (US)

(72) Inventors: Brian Frank Lewis, Terre Haute, IN (US); Bernard Michael McGarvey, Ft. Myers Beach, FL (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/495,774

(22) PCT Filed: Oct. 11, 2018

(86) PCT No.: PCT/US2018/055331
§ 371 (c)(1),
(2) Date: Sep. 19, 2019

(87) PCT Pub. No.: WO2019/079088
PCT Pub. Date: Apr. 25, 2019

(65) Prior Publication Data
US 2020/0016324 A1   Jan. 16, 2020

Related U.S. Application Data

(60) Provisional application No. 62/573,843, filed on Oct. 18, 2017.

(51) Int. Cl.
*G01N 33/00* (2006.01)
*A61M 5/31* (2006.01)
*G01N 11/00* (2006.01)

(52) U.S. Cl.
CPC ........... *G01N 33/00* (2013.01); *A61M 5/3129* (2013.01); *A61M 2005/3131* (2013.01);
(Continued)

(58) Field of Classification Search
CPC ............... G01N 33/00; G01N 11/00; G01N 2033/0078; A61M 2209/02
See application file for complete search history.

(56) References Cited

U.S. PATENT DOCUMENTS 10,269,117 B1 *   4/2019   Matayoshi ............. G01N 21/90
2013/0209766 A1 *   8/2013   Felts .................. A61M 5/31513
                                                                                   428/216
(Continued)

FOREIGN PATENT DOCUMENTS

WO         0173363        10/2001
WO      2017086366         5/2017

*Primary Examiner* — Nathaniel J Kolb
(74) *Attorney, Agent, or Firm* — Marion Daniel Spillman

(57) ABSTRACT

A centrifugation approach used to accelerate current empirical methods used to investigate silicone drainage in syringes is disclosed. A siliconized syringe is placed into a holder of a centrifuge in a predefined orientation. Centrifugation of the syringe is activated at a predetermined G rate and for a period of intended simulation time and is ended as that time elapses. The time can be a function of intended simulation time, acceleration due to gravity, square of centrifuge revolution rate, and distance from center of rotor hub to matching point on the syringe barrel. One or more injection functionality parameters of the syringe is assessed after the elapsed period of time. A bucket fixture for retaining one or more syringes in the predefined orientation is also disclosed.

18 Claims, 13 Drawing Sheets

(52) U.S. Cl.
CPC ......... *A61M 2209/02* (2013.01); *G01N 11/00* (2013.01); *G01N 2033/0078* (2013.01)

(56) References Cited

U.S. PATENT DOCUMENTS

| | | | |
|---|---|---|---|
| 2015/0335823 A1* | 11/2015 | Weikart | C23C 16/045 604/187 |
| 2017/0108451 A1* | 4/2017 | Gertz | A61L 31/10 |
| 2019/0231986 A1* | 8/2019 | Devaraneni | B01D 39/18 |

* cited by examiner

ACCELERATED TESTING METHOD OF SILICONE DRAINAGE IN SYRINGES

CROSS-REFERENCE TO RELATED APPLICATIONS

This application claims benefit to U.S. provisional application No. 62/573,843, filed Oct. 18, 2017, which is hereby incorporated herein by reference in its entirety.

BACKGROUND

The present disclosure relates to accelerated testing methods and systems of silicone drainage in medical devices, and in particular, syringes used in a medication delivery device.

Syringes are used to deliver medication. Syringes include a barrel extending between a flange and a shoulder that leads to a needle hub. The medication may be contained within the barrel and dispensed by movement of a piston slidable along the inner walls of the barrel. When stored, the syringes have the needle end facing up and the flange end pointing down. Silicone or other substances are disposed along the inner walls of the syringe for lubrication and extended sealing. After syringes have been siliconized, the syringes may be stored for significant periods of time. During this storage time, the initial distribution of silicone may change as the silicone drains from the top to the bottom (that is, from the needle end toward the flange end) under gravity. Understanding these changes due to silicone drainage is necessary to appreciate the effects of changes in silicone distribution of empty syringes during storage on injection functionality and in silicone particulate levels in prefilled syringes once filled with medication. Currently, only empirical methods are available for these types of assessments and the methods require studies with extended durations to document the effects of empty component storage and filled syringe storage over time. These studies can require substantial duration. As an example, it can take over 6 years to study the combined effects of the maximum allowed empty and filled storage times for the syringes, if up to four years for the storage of empty syringe barrels before filling is desired and up to two years for the storage of filled syringes is desired after the maximum empty storage has elapsed. Accordingly, there is a need to understand the silicone drainage from a first principles perspective and to use this understanding to identify a way to accelerate the studies so that useful information can be created in a much shorter time than 6 years and/or overcome one or more of these and other shortcomings of the prior art.

SUMMARY OF THE DISCLOSURE

In one embodiment, a testing method for accelerating silicone drainage rate for a siliconized syringe is disclosed. The method includes one or more of the following steps: Placing a syringe including a film of silicone in a predefined orientation into a centrifuge holder of a centrifuge system. The syringe includes a needle end and an opposite, flange end. The predefined orientation of the syringe includes the flange end being disposed farther away from a center axis of the centrifuge system than the needle end or the needle end being disposed farther away from said center axis of the centrifuge system than the flange end. Activating a centrifugation of the centrifugation holder of the centrifuge system with the syringe at a predetermined G-rate and for a predetermined period of a time. Ending the centrifugation of the centrifugation holder with the syringe after the period time has elapsed. Assessing one or more injection functionality parameters of the syringe after the elapsed period of time.

In another embodiment, a testing method for accelerating silicone drainage rate for a siliconized syringe is provided. The method includes one or more of the following steps: Placing a syringe including a film of silicone in a predefined orientation into a centrifuge holder of a centrifuge system. The syringe includes a needle end and an opposite, flange end. The predefined orientation of the syringe includes the flange end being disposed farther away from a center axis of the centrifuge system than the needle end or the needle end being disposed farther away from the center axis of the centrifuge system than the flange end.

Activating a centrifugation of the centrifugation holder of the centrifuge system with the syringe at a predetermined G-rate and for a predetermined period of a time (tfc), wherein the period of time (tfc) is expressed:

$$\frac{t_{fg}}{t_{fc}} = \frac{(r_c + zL_F)\omega^2}{g}$$

where $t_{fg}$ is a gravity drainage time to be simulated and $t_{fc}$ is the centrifuge run time at speed $\omega$ in the centrifuge system with a rotor arm length of $r_c$, a matching point of z, a length of the syringe of $L_F$, and g is an acceleration due to gravity. Ending the centrifugation of the centrifugation holder with the syringe after the period time has elapsed.

In yet another embodiment, a syringe testing apparatus for a centrifuge system is disclosed. The syringe includes a barrel with a barrel diameter and a flanged end diameter greater than the barrel diameter. The apparatus includes a body defining a plurality of cells extending between an upper end and a lower end of the body. Each of the cells includes a diameter sized to receive a barrel of the syringe but not a flange of the syringe. A base plate includes a plurality of recesses. Each of the recesses is arranged in coaxial alignment with a corresponding cell of the body. Each of the recesses includes a diameter sized greater than the diameter of the cell, and a depth sized to capture a thickness of the flange of the syringe. The base plate includes attachment features for secure attachment to the lower end of the body.

BRIEF DESCRIPTION OF THE DRAWINGS

Additional embodiments of the disclosure, as well as features and advantages thereof, will become more apparent by reference to the description herein taken in conjunction with the accompanying drawings. The components in the figures are not necessarily to scale. Moreover, in the figures, like-referenced numerals designate corresponding parts throughout the different views.

DETAILED DESCRIPTION

Figure 1:
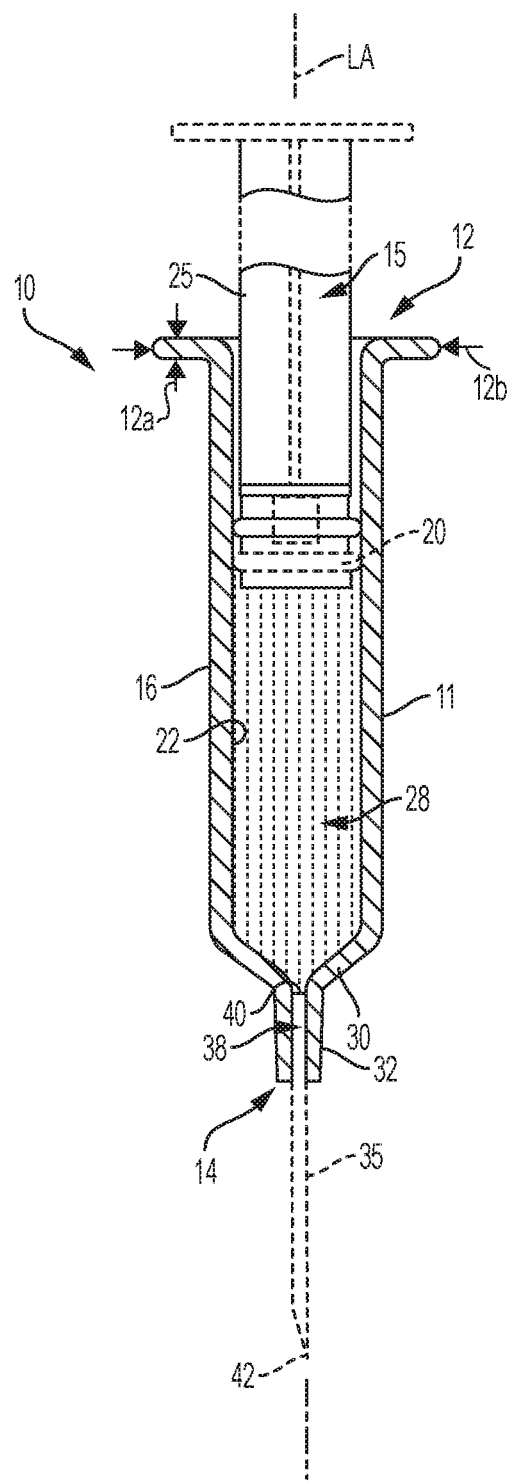
FIG. 1 is a side cross-sectional view of an embodiment of a filled and assembled manual prefilled syringe.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

After syringes have been siliconized, the syringes may be stored for significant periods of time (where the syringes are typically stored with the needle end up and the flange end down, although aspects of the present disclosure are applicable to syringes stored with flange end up and needle end down, or any orientation in between). During this storage time the initial distribution of silicone may change as the silicone drains from the top to the bottom under gravity. Such changes can be understood if the long term performance of the syringes is to be controlled. This disclosure describes a centrifugation approach used to accelerate the current empirical methods that are used to investigate silicone drainage in syringes, which currently takes years to complete. In one form, a method to accelerate aging of siliconized syringes using a centrifuge is described. Fundamental predictive relationships for actual aging and simulated aging by centrifugation are related. Applying the method of centrifugation is useful for rapidly simulating syringe functionality change after long-term storage in the empty state.

By way of illustration, the syringe alone may be used as a medication delivery device or may be used in conjunction with another device which is used to set and to deliver a dose of a medication, such as pen injectors, infusion pumps and auto-injectors. The medication may be any of a type that may be delivered by such a medication delivery device. Syringes may be provided empty or with a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

An exemplary syringe 10 is illustrated in FIG. 1. The syringe 10 includes a syringe body 11 extending about a longitudinal axis LA between an open proximal flange end 12 and a distal needle end 14. A plunger rod and piston assembly 15 may be mounted to a cylindrical barrel 16 of body 11 through the open flange end 12. Flange end 12 is shown projecting radially outward beyond outer diameter of the syringe barrel 16. A piston 20 is in sealably and slidably disposed along an interior surface 22 of the barrel 16. A plunger rod shaft 25 is an elongated member coupled to the piston 20. The plunger rod shaft 25 projects proximally beyond the flange end 12 and is adapted to be pushed distally from an extended position (shown in FIG. 1) in order to move the piston 20 distally within the barrel 16 to dispense medication from a chamber 28 defined within the syringe barrel between the piston 20 and needle end 14. The cylindrical barrel 16 extends from the flange end 12 to a transition or shoulder 30 that leads to a reduced cross-sectional area syringe hub 32 that is smaller than the cylindrical barrel 16. The flange end 12 may project radially outward farther than cylindrical barrel portion 16. The syringe body 11 may be made of glass, at least partially of glass, such as a glass barrel having a plastic flange at its proximal end, or a polymer suitable for syringe operation.

The syringe hub 32 may include a needle extending distally therefrom or may be adapted to receive an attachable needle assembly (not shown). A distal end of the syringe barrel 16 along the shoulder portion 32 includes a passageway 38 which is in fluid communication with the chamber 28. An elongate needle cannula 35 (shown in dashed) includes a lumen extending therethrough between its proximal and distal ends 40, 42. Proximal end 40 of the needle cannula 35 is coupled to the distal needle end 14 of the syringe barrel 16 through the passageway 38 to place the needle lumen in fluid communication with the chamber 28. In illustrated example, the needle cannula 35 is securely attached to the syringe body 11 through the use of adhesives or other attachment means. In other examples, the needle may be removably attached to the syringe body 11 such as through needle attachment hub which is permanently attached to the needle cannula and frictionally attached around needle hub 32 of the syringe. For the purposes of this disclosure, the testing of the syringes may involve only the syringe body of syringe 10, with the plunger and piston assembly 15 and needle 35 omitted, which is why these elements are shown dashed.

An exemplary method to accelerate the testing of silicone drainage in syringes is to use centrifugation as a way to replace gravity forces with centrifugal forces that are higher than gravity forces. The resulting silicone drainage from centrifugal forces can be strongly correlated to drainage resulting from gravity, and a centrifugation test can be used to replace the long period of gravity studies, potentially changing the study from years to hours. To this end, a mathematical model that allows for both drainage under gravity and centrifugal forces was created and used to analyze a set of test data from a centrifugation syringe silicone drainage test. This model leads to a quasilinear first order Partial Differential Equation (PDE) that can be solved numerically.

A mathematical model was developed for falling thin film flow drainage in the syringe barrels. The main assumptions involved in building this model are: (1) The film is thick enough that the continuum approach to fluid dynamics is applicable. For example, a value of 1 μm (micron) may be given as a lower bound on the typical length scale for a liquid system in order for the continuum hypothesis to be valid, see Hunter, S. C., 1976, "Mechanics of Continuous Media", Ellis Horwood Limited Publisher, ISBN 85312-042-0, although testing has demonstrated less than 1 micron. To the contrary, the silicone film in syringes can be much smaller than 1 μm so the validity of extending the continuum approach to such small films was determined when the model results were compared to experimental results, such as shown, for example, in FIG. 12. (2) The film thickness is small. This means that velocities are small, leading to low Reynolds numbers, and it means that velocity gradients in the downward direction will be small. (3) The friction on the outside surface of the silicone layer is zero, whether the syringe is empty or filled with liquid. In the former case the outer silicone surface is in contact with air and in the latter case the silicone layer is in contact with the liquid product material. (4) Surface tension effects can be ignored. The disclosure uses the following nomenclature in Table 1:

TABLE 1

| Variable | Description |
|---|---|
| D, $D_C$ | Inside diameter of the syringe |
| $L_f$ | Length of syringe covered by silicone layer measuring device |

TABLE 1-continued

| Variable | Description |
|---|---|
| $r_C$ | Radius of the centrifuge arm to the initial point silicone measurement |
| T | Time |
| $t_o$ | Time that the initial silicone distribution profile in the z-direction is determined |
| $t_f$ | Total time that the model runs for |
| T_Fct | Parameter that determines where along the barrel the centrifugal forces are calculated so that the centrifugation time is equivalent to the drainage time under gravity. |
| Z | Distance along the length of the syringe barrel |
| G | Acceleration under gravity |
| R | The internal radius of the syringe barrel such that R = D/2 |
| $\alpha(z)$ | Acceleration function defined by Equation (2.2). |
| $\beta$ | Parameter that determines the drainage model in the model – $\beta = 0$ indicates drainage under gravity, $\beta = 1$ indicates drainage under centrifugal forces |
| $\gamma$ | Dimensionless value that identifies the inner radius of the silicone layer such that $\gamma = 1 - \delta/R$ |
| $\delta$ | Thickness of the silicone layer |
| $\Psi$ | Dimensionless value representing the thickness of the silicone layer |
| $\rho$ | Density of the silicone |
| $\omega$ | Angular rotation speed of the centrifuge in radian/s |
| $\mu$ | Dynamic viscosity of the silicone |
| μm | Micrometer, micron |
| $\eta$ | Kinematic viscosity of the silicone |

Figure 2:
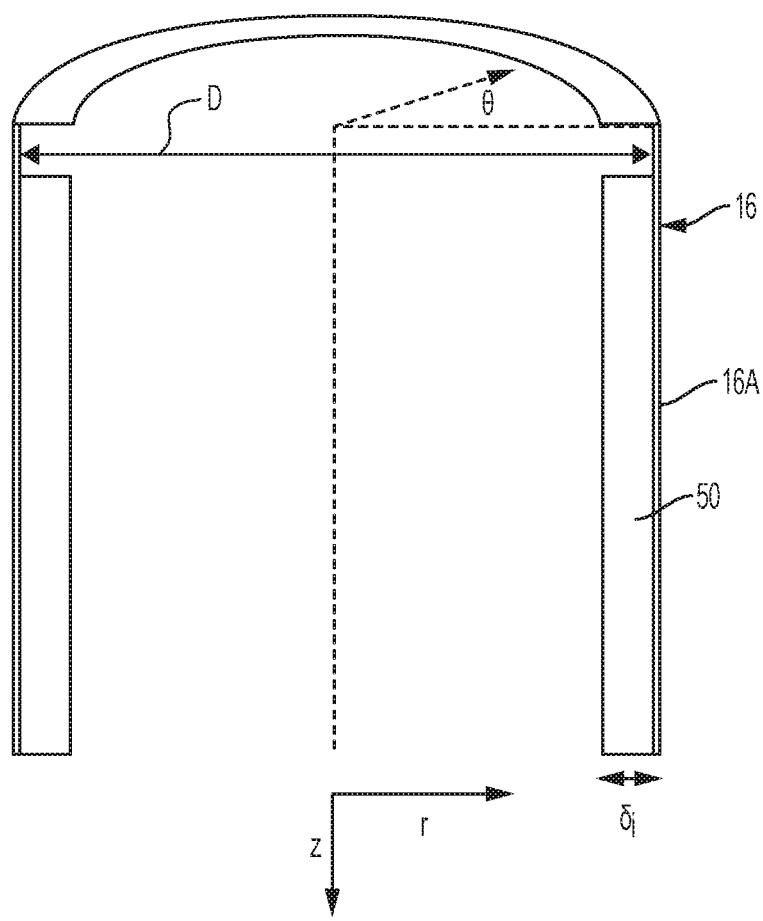
FIG. 2 is a cross-sectional partial detail of a wall portion of the syringe in FIG. 1, depicting the syringe wall with a film of silicone.

The model developed covers both the case of gravity induced drainage and centrifugal force induced drainage from a cylindrically shaped syringe, such as the syringe 10, with a film 50 initially of size $\delta_o(z)$, as shown in FIG. 2, disposed along a wall 16A of the syringe barrel 16 (see Holland, F. A., 1973, "Fluid Flow for Chemical Engineers", Edward Arnold Ltd, ISBN 0-7131-3301-5).

In general the initial thickness of film 50 will vary along the length of the syringe barrel 16, although in FIG. 2 it is shown as a constant initial thickness. Note that the z direction is taken as the downward direction, in the same direction as gravity and the centrifugal force. The assumption that the syringe barrel 16 surrounding the chamber 28 is a perfect cylinder, that is, having a constant inside diameter D, that allows the use of cylindrical coordinates (z, r, θ), as shown in FIG. 2. However, any coordinate conventions, such as Cartesian coordinates, may be used. It is assumed that no dependent variable in the model is a function of angle (θ). At time 0 (zero), the film 50 will begin to drain downwards under the action of gravity/centrifugal forces. A velocity will develop in both the axial (z) and radial (r) directions. If it is assumed that the film 50 is initially a thin film, the velocities generated will be small and so the film's Reynolds number will be small. Under these conditions, the flow becomes "developed" very quickly and so it is assumed that the velocity in the r direction is 0 (zero). Further, in the equation for the z velocity, it can be assumed that the inertial terms can be neglected as well as any pressure gradients in the z direction. The velocity in the z direction is then only a function of r and remains steady. Since there is only one velocity component, $u_z$, velocity will be referred to as u, since there can be no confusion as to which component of velocity it refers. Using these assumptions, the momentum balance in the z-direction (from Navier-Stokes equations) can be simplified to:

$$0 = \mu\left[\frac{1}{r}\frac{\partial}{\partial r}\left(r\frac{\partial u}{\partial r}\right)\right] + \rho g(z) \quad (A.1)$$

where $\mu$ is the dynamic viscosity of the liquid, $\rho$ is the density of the liquid, and g is the gravity/centrifugal force. For gravity flow, $g(z)$ is a constant g, but for the centrifuge flow, $g(z)$ is expressed as follows:

$$g(z) = (r_c + z)\omega^2 \quad (A.2)$$

where $r_c$ is the radius of the centrifuge arm, $\omega$ is the angular velocity of the centrifuge in radian/sec and z measures the distance from the end of the centrifuge arm along the syringe.

Given that velocity u is a function of r only, Equation (A.1) can be written with ordinary derivatives rather than partial derivatives. This gives $$\frac{d}{dr}\left(r\frac{du}{dr}\right) = -\alpha(z)r \text{ where } \alpha(z) = \frac{\rho g(z)}{\mu}. \quad (A.3)$$

The equation for $\alpha(z)$ can be written as:

$$\alpha(z) = \frac{\rho}{\mu}[(1-\beta)g + \beta(r_C + z)\omega^2] \quad (A.4)$$

Where $\beta$ represents the influence of centrifugal force such that $\beta=0$ indicates that the flow is under gravity and $\beta=1$ indicates that the flow is under centrifugal forces. Combining Equations (A.3) and (A.4) and integrating the combined equation and applying the boundary conditions shown in Equations (A.6) and (A.7). In the following, the explicit dependence of acceleration $\alpha$ on direction z will be assumed and so $\alpha(z)$ will be written simply as acceleration $\alpha$.

Equation (A.3) can be integrated twice to yield an expression for velocity as a function of density, acceleration, viscosity, and layer thickness once the appropriate boundary conditions are applied. Here, the boundary conditions are:

$$r\frac{du}{dr} = -\frac{\alpha}{2}r^2 + C_1 \quad (A.5)$$

where $C_1$ is a constant of integration. $C_1$ can be found from one of the boundary conditions for the velocity u, which is that the shear stress at the boundary of the film 50 is zero. Mathematically this translates to:

$$\frac{du}{dr} = 0$$

when $$r = \frac{D}{2} - \delta$$

(equivalent to $r=\gamma R$) and $\gamma=(D-2\delta)/D$
where D is the inside diameter of the syringe barrel 16 surrounding the chamber 28 and $\delta$ is the thickness of the film 50.

The second boundary condition is that there is no slip of the liquid at the inner surface of the glass syringe barrel. This gives
u=0 when $$r = \frac{D}{2}$$

(equivalent to r=R)
Integrating Equation (A.3) and applying boundary conditions in Equations (A.6) and (A.7) yields:

$$u = -\frac{\alpha}{4}r^2 + \frac{\alpha}{8}\gamma^2 D^2 \ln(r) + C_2 = \quad (A.8)$$
$$-\frac{\alpha}{4}r^2 + \frac{\alpha}{8}\gamma^2 D^2 \ln(r) + \frac{\alpha}{16}D^2 - \frac{\alpha}{8}\gamma^2 D^2 \ln\left(\frac{D}{2}\right) =$$
$$\frac{\alpha}{16}D^2\left[1 - \left(\frac{2r}{D}\right)^2 + 2\gamma^2 \ln\left(\frac{2r}{D}\right)\right]$$

Now the velocity profile as a function of r is known, the flowrate of the film 50 can be calculated when the thickness is $\delta$. The flowrate Q in the z direction is given by:

$$Q = \int_{\frac{D}{2}-\delta}^{\frac{D}{2}} 2\pi r u\, dr = 2\pi \int_{\frac{\gamma D}{2}}^{\frac{D}{2}} r u\, dr. \quad (A.9)$$

Substituting Equation (A.8) into Equation (A.9) gives:

$$Q = \frac{\pi\alpha}{8}D^2 \int_{\frac{\gamma D}{2}}^{\frac{D}{2}}\left[r - \frac{4r^3}{D^2} + 2\gamma^2 r\ln\left(\frac{2r}{D}\right)\right] dr. \quad (A.10)$$

The integral in Equation (A.10) can be evaluated to yield:

$$Q = \frac{\pi\alpha D^4}{128}[1 - 4\gamma^2 + 3\gamma^4 - 4\gamma^4\ln(\gamma)] = \quad (A.11)$$
$$\frac{\pi\alpha D^4}{128}s(\gamma) \text{ where } s(\gamma) = 1 - 4\gamma^2 + 3\gamma^4 - 4\gamma^4\ln(\gamma)$$

where, by the definition of dimensionless variable $\gamma$, see Equation (A.7), $\gamma<1$.

Now that the equation for the flowrate Q is provided, as a function of the film thickness, $\delta$, the unsteady state evolution of the film thickness $\delta$ as a function of z can be evaluated. An unsteady state mass balance over the slice between z and z+$\Delta$z can be written as $$\frac{\partial}{\partial t}[\text{Volume in slice}] = Q_z - Q_{z+\Delta z} \quad (A.12)$$

Rate of Accumulation = Rate In − Rate Out.

The volume in the slice, $\Delta V$, is given by $$\Delta V = \left\{\pi\left(\frac{D}{2}\right)^2 - \pi\left(\frac{D}{2} - \delta\right)^2\right\}\Delta z. \quad (A.13)$$

Equation (A.13) can be simplified to $$\Delta V = \pi (D\delta - \delta^2)\Delta z. \tag{A.14}$$

Substituting Equation (A.14) into Equation (A.12) gives as follows.

$$\frac{\partial}{\partial t}[\pi(D\delta - \delta^2)\Delta z] = \tag{A.15}$$

$$Q_z - Q_{z+\Delta z} \Rightarrow \left\{\frac{\partial}{\partial t}[\pi(D\delta - \delta^2)\Delta z]\right\}\Delta z = Q_z - Q_{z+\Delta z}$$

Dividing both sides of Equation (A.26) by $\Delta z$ and taking the limit as $\Delta z \to 0$, gives $$\frac{\partial}{\partial t}[\pi(D\delta - \delta^2)\Delta z] = -\frac{\partial Q}{\partial z}. \tag{A.16}$$

which can be simplified to $$\pi(D - 2\delta)\frac{\partial \delta}{\partial t} = -\frac{\partial Q}{\partial z}. \tag{A.17}$$

Since film thickness $\delta \ll$ inside diameter D of the syringe barrel, Equation (A.17) can be simplified further:

$$\pi D \frac{\partial \delta}{\partial t} + \frac{\partial Q}{\partial z} = 0 \tag{A.18}$$

where Q is given by Equation (A.11). It is now convenient to introduce another dimensionless $\psi$ where:

$$\psi = 1 - \gamma = \frac{\delta}{\frac{D}{2}} \text{ so that } \delta = \frac{D}{2}\psi. \tag{A.19}$$

Equation (A.18) now becomes:

$$\frac{\pi D^2}{2}\frac{\partial \psi}{\partial t} + \frac{\partial Q}{\partial z} = 0. \tag{A.20}$$

Substituting Equation (A.11) for Q into Equation (A.20) gives:

$$\frac{\pi D^2}{2}\frac{\partial \psi}{\partial t} + \frac{\pi D^4}{128}\frac{\partial (\alpha(z)s(\psi))}{\partial z} = 0 \text{ where} \tag{A.21}$$

$$s(\psi) = 1 - 4(1-\psi)^2 + 3(1-\psi)^4 - 4(1-\psi)^4 \ln(1-\psi)$$

Equation (A.21) can be reduced to:

$$\frac{\partial \psi}{\partial t} + \frac{D^2}{64}\left[s(\psi)\frac{d\alpha(z)}{dz} + \alpha(z)\frac{ds(\psi)}{d\psi}\frac{\partial \psi}{\partial z}\right] = 0. \tag{A.22}$$

In Equation (A.22) the fact that $\Psi$ is a function of z and $s(\psi)$ is a function of z as well. The ordinary derivatives in Equation (A.22) can be found from Equations (A.4) and (A.21)

$$\frac{d\alpha(z)}{dz} = \frac{\rho}{\mu}[\beta\omega^2] \tag{A.23}$$

$$\frac{ds(\psi)}{d\psi} = 8(1-\psi) - 8(1-\psi)^3 - 16(1-\psi)^3 \ln(1-\psi) \tag{A.24}$$

The equations for $s(\psi)$ and its derivative can be simplified since film thickness $\delta \ll$ inside diameter D and so $\psi \ll 1$. The function $\ln(1-x)$ can be expanded as $$\text{Ln}(1-\psi) = -\psi - \frac{\psi^2}{2} - \frac{\psi^3}{3} - \frac{\psi^4}{4} \ldots \tag{A.25}$$

Expanding all the terms in the equations for $s(\psi)$ and its derivative gives:

$$s(\psi) = 16\frac{\psi^3}{3} - 19\frac{\psi^4}{3} + 4\psi^5 \ldots \tag{A.26}$$

$$\frac{ds(\psi)}{d\psi} = 16\psi^2 - 64\frac{\psi^3}{3} + 8\psi^4 \ldots \tag{A.27}$$

These equations can be simplified to the following by using the leading term in the equations.

$$s(\psi) = 16\frac{\psi^3}{3} \tag{A.28}$$

$$\frac{ds(\psi)}{d\psi} = 16\psi^2 \tag{A.29}$$

Substituting into Equation (A.22) and simplifying leads to $$\frac{\partial \psi}{\partial t} + \left(\frac{D^2}{4}\alpha(z)\psi^2\right)\frac{\partial \psi}{\partial z} = -\frac{D^2}{12}\left[\frac{d\alpha(z)}{dz}\right]\psi^3. \tag{A.30}$$

Figure 4:
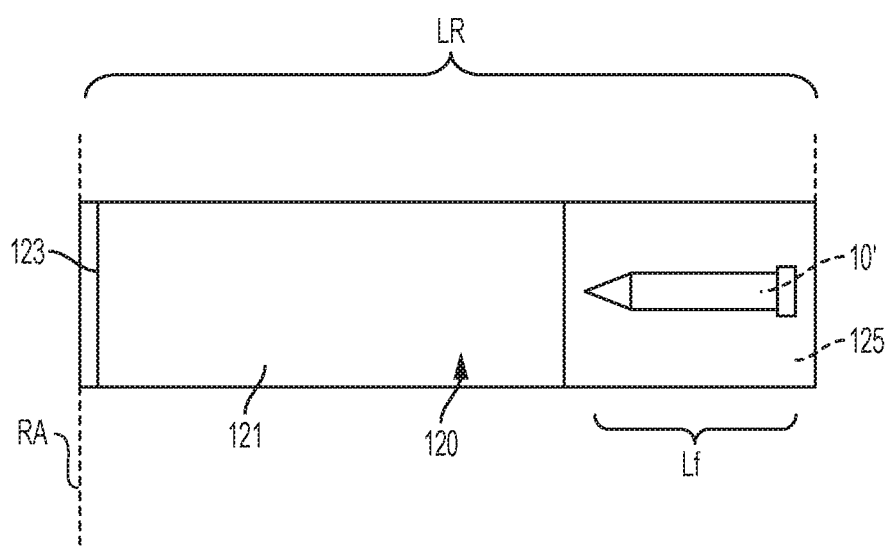
FIG. 4 depicts a syringe's orientation and length relative to that of a rotor arm of the centrifuge system in FIG. 3.

The final step in the model is to make it dimensionless in direction z and time, t, by normalizing z by $L_f$ (the length of the syringe from the tip nearest the centrifuge center where the film thickness measurements start to the other end of the syringe, as shown in FIG. 4) and $t_f$, the total time horizon of the model. This leads to the final form of the model equation:

$$\frac{\partial \psi}{\partial t} + \frac{t_f}{L_f}\left(\frac{D^2}{4}\alpha(z)\psi^2\right)\frac{\partial \psi}{\partial z} = -t_f\frac{D^2}{12}\left[\frac{d\alpha(z)}{dz}\right]\psi^3 \tag{A.31}$$

where now z and t are the dimensionless z and t variables and the model runs from $0 \le z \le 1$ and $0 \le t \le 1$. The equation for $\alpha(z)$ in the dimensionless z form becomes:

$$\alpha(z) = \frac{\rho}{\mu}[(1-\beta)g + \beta(r_C + zL_f)\omega^2] \tag{A.32}$$

and for the derivative it becomes:

$$\frac{d\alpha(z)}{dz} = \frac{\rho}{\mu}[\beta L_f \omega^2]. \quad (A.33)$$

The details involved in the derivation of the model equation (1.0) are given in Equations A.1 to A.33.

$$\frac{\partial \psi}{\partial t} + \left(\frac{D^2}{4}\alpha(z)\psi^2\right)\frac{\partial \psi}{\partial z} = -\frac{D^2}{12}\left[\frac{d\alpha(z)}{dz}\right]\psi^3 \quad (1.0)$$

The final step in the model is to make it dimensionless in z and t by normalizing z by Lf (the length of the syringe from the tip nearest the centrifuge center where the film thickness measurements start to the other end of the syringe) and tf, the total time horizon of the model. Dimensionless z and t lead to the final form of the mathematical model equation:

$$\frac{\partial \psi}{\partial t} + \frac{t_f}{L_f}\left(\frac{D^2}{4}\alpha(z)\psi^2\right)\frac{\partial \psi}{\partial z} = -t_f\frac{D^2}{12}\left[\frac{d\alpha(z)}{dz}\right]\psi^3. \quad (2.1)$$

The model runs from 0<=z<=1 and 0<=t<=1. The equation for α(z) in the dimensionless z form becomes:

$$\alpha(z) = \frac{\rho}{\mu}[(1-\beta)g + \beta(r_C + zL_f)\omega^2] \quad (2.2)$$

and for the derivative it becomes:

$$\frac{d\alpha(z)}{dz} = \frac{\rho}{\mu}[\beta\omega^2]. \quad (2.3)$$

Note that in Equation (2.3), the derivative is with respect to the original z, not the dimensionless form of z. Hence the $L_f$ does not appear in Equation (2.3). The form of the model in Equation (2.1) is that of a wave equation where the wave speed $V_W$ is given by:

$$V_W = \frac{t_f}{L_f}\left(\frac{D^2}{4}\alpha(z)\psi^2\right) = \frac{t_f}{L_f}\left[\frac{D^2}{4}\frac{\rho}{\mu}((1-\beta)g + \beta(r_C + zL_f)\varpi^2)\right]\psi^2 \quad (2.4)$$

Thus, the speed at which the silicone moves along the syringe barrel is directly proportional to $t_f$, silicone density ρ, the acceleration g when under gravity, and $r_c$ when under centrifugal forces. The wave speed is proportional to the square of inside diameter D and ω. The wave speed is inversely proportional to $L_f$. All of these variables are constant for a given configuration and so these variables will not change the wave speed for a syringe being centrifuged for simulated aging. The variables that will change are z and φ. The wave speed increases as z increases which reflects the longer radius for the centrifugal force. The wave speed also decreases as φ decreases in a quadratic way, whether this is gravity or centrifugal force driven. To this end, as the movement of the silicone proceeds the value of φ tends to fall. The rate at which φ falls depends on φ itself so the biggest change in φ occurs at the earlier times once the movement has started.

The model also indicates how the time should be scaled in order to see the same effect between gravity and centrifugal flow. Denoting the value of $t_f$ as $t_{fg}$ for gravity flow and $t_{fc}$ for centrifugal flow, the ratio of $t_{fc}$ to $t_{fg}$ is given by:

$$\frac{t_{fg}}{t_{fc}} = \frac{(r_C + zL_f)\omega^2}{g} \quad (2.5)$$

In Equation (2.5) a value of z must be chosen, remembering that 0<=z<=1. If z is set=0 to do the scaling in Equation (2.5), the centrifugal force on the entire silicone layer will be underestimated and so the centrifuging time equivalent to a time under gravity will be overestimated. The opposite will occur if z is set to 1. Given that the dependence of the centrifugal force is linear in z, the best value of z to use is likely to be closer to 0.5. If the wave speed depended on the value of φ in a linear way then the best value to use would be 0.5 exactly. In the Example below, the assertion that z=0.5 is better than z=0 or z=1 will be tested. A parameter T_Fct can be defined and used to rewrite Equation (2.5) as:

$$\frac{t_{fg}}{t_{fc}} = \frac{(r_C + T\_Fct * zL_F)\omega^2}{g} \quad (2.6)$$

T_Fct=0.0 will be designated as the Low condition, T_Fct=0.5 will be designated as the Mid condition, and T_Fct=1.0 will be designated as the High condition. These conditions at which the tip (T_Fct=1.0), middle (0.5), and flange (0.0) points are subjected to, such that the aging time matches the corresponding point along the syringe.

Simulations using the model presented here in Equations (2.1) and (2.2) have reproduced experimental drainage in syringes under centrifugal forces.

This model also shows that, based on the first principles of fluid flow under gravity and centrifugal forces, it is possible to scale the time require for a given amount of silicone drainage using Equation (2.6). Simulations have shown that of the three conditions Low, Medium, and High described above, the most accurate scaling for silicone flow is produced by a value of T_Fct=0.5. This matching point can be varied at the selection of the operator using this formula. Matching various points may be preferred if different aspects of the syringe behavior need to be understood. An example can be the use of a spring-driven autoinjector where a thinner silicone layer at the tip might be of more concern due to the higher glide force it may create or increased injection times that may be observed with self-injection devices. In that case it would be better to select a T_Fct of 0 to better match this point.

Because the centrifugal force is a linear function of the distance from the center of the centrifuge but the acceleration due to gravity is effectively a constant, a small ratio of the centrifuge arm length to syringe barrel length will lead to in accurate scaling. The system described here refers to systems where this ratio is at least 4:1.

Note that one skilled in the art can apply other approaches to developing the model based on the key assumptions described above to achieve similar modelling results while the principles are based on the key assumptions and the approach outlined in the steps that follow the model development. For example, a model can be developed using Cartesian coordinates and assuming that because the film is very thin, the flow is planar rather than cylindrical. In this case, equation (A.3) becomes:

$$\frac{d^2 u}{dy^2} = -\alpha(z) \quad (B.1)$$

and if we assume that the glass surface corresponds to y=0, the two boundary conditions equivalent to (A.6) and (A.7) become:

$$\frac{du}{dy} = 0 \text{ at } y = \delta \quad (B.2)$$

and u=0 at y=0 (B.3)

Here Equations (B.2) and (B.3) are equivalent to (A.6) and (A.7) in the cylindrical coordinate model.

Integrating twice and applying the boundary conditions yields the equivalent to equation (A.8):

$$u = -\frac{\alpha(z)y^2}{2} + \alpha(z)\delta y \quad (B.4)$$

The equivalent to equation (A.10) becomes:

$$Q = \pi D \int_0^\delta \left( -\frac{\alpha(z)y^2}{2} + \alpha(z)\delta y \right) dy \quad (B.5)$$

Evaluating the integral yields the result that is equivalent to (A.11):

$$Q = \frac{\pi D \alpha(z) \delta^3}{3} \quad (B.6)$$

The volume slice described in (A.14) becomes:

$$\Delta V = \pi D \delta \Delta z \quad (B.7)$$

This means that Equation (A.18) is exactly the same here:

$$\pi D \frac{\partial \delta}{\partial t} + \frac{\partial Q}{\partial z} = 0 \quad (B.8)$$

Because flat geometry is assumed, the dimensionless term Ψ is less meaningful. Therefore, the equivalent to equation (2.4) is displayed below in terms of δ and not Ψ:

$$\frac{d\delta}{dt} + \alpha(z)\delta^2 \frac{d\delta}{dz} = -\frac{\rho \beta \omega^2 \delta^3}{3\mu} \quad (3.0)$$

Equation (3.0) can be integrated numerically in time to obtain a relationship for δ(z,t), given an initially known silicone distribution of δ(z,t$_0$).

EXAMPLE

In a preliminary test, a set of 20 syringes, of a configuration such as the ones described herein, were divided into two groups. The first group was designated as samples 1 to 10 and the second as samples 11 to 20. The samples 1 to 10 were centrifuged for a time equivalent to 2 years of gravity flow and the samples 11 to 20 were centrifuged for a time equivalent of 1 year of gravity flow. A layer film including silicone was measured pre and post centrifugation using various test methods, such as, for example, an analytical method to characterize sprayed-on silicone oil layer thickness distribution in empty prefilled syringes using instruments, also referred to as a RapID. The measurement device reported the thickness at z distances of 0 to 49 mm in 1 mm increments. At each z point the device measures 9 points along the circumference. These 9 points were averaged to give the average silicone layer thickness at each z point.

Figure 3B:
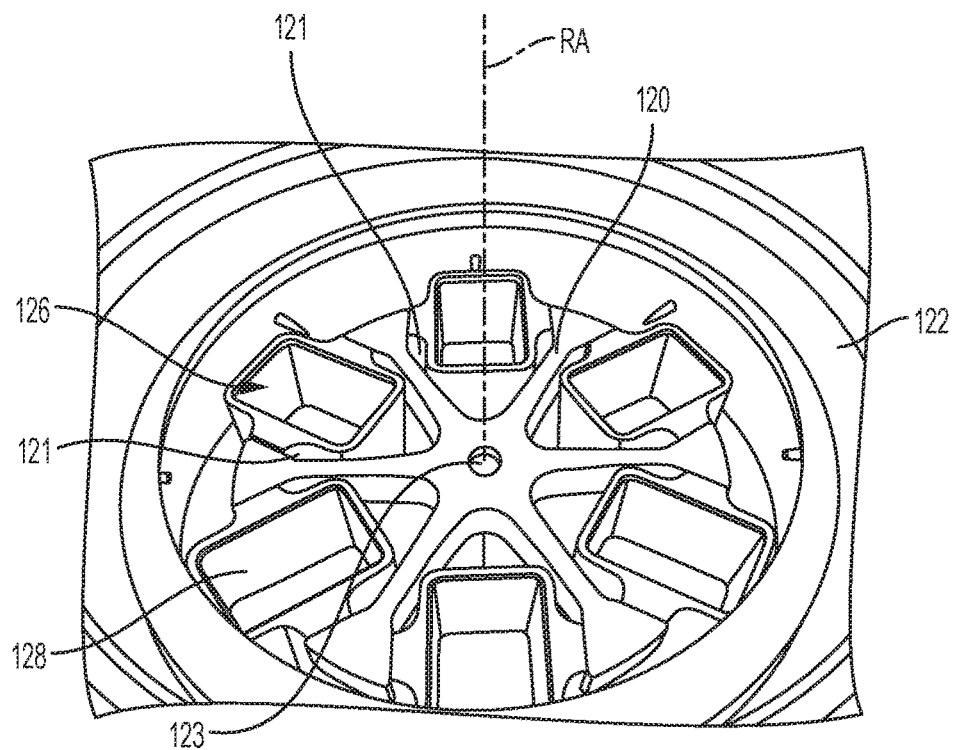
FIG. 3B is a top view of the centrifuge system in FIG. 3A.
Figure 3A:
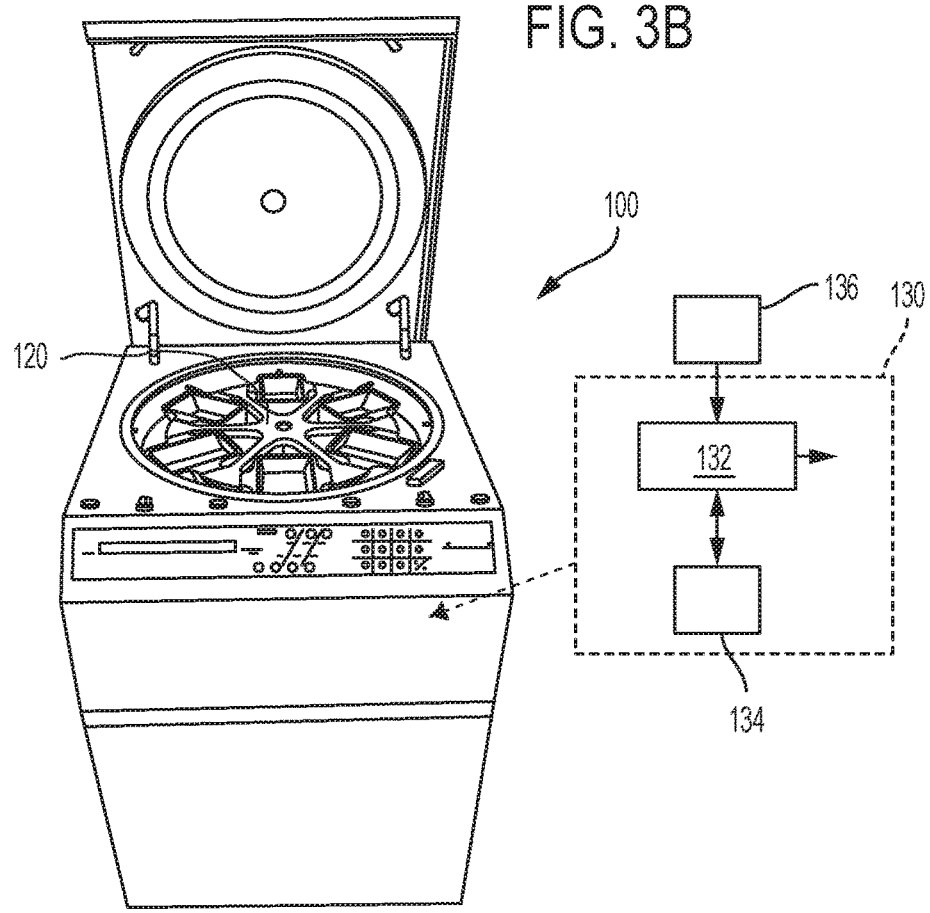
FIG. 3A depicts an exemplary centrifuge system used for an accelerated testing of silicone drainage in syringes.

Any centrifuge system may be used for the test. In one example, the centrifuge system 100 includes a Jouan KR4-22 (S/N 403100041) centrifuge, such as shown in FIG. 3A. The centrifuge system 100 includes one or more fixture buckets configured to hold syringes. With additional reference to FIG. 3B, system 100 includes a rotor 120 rotatable relative to a system housing 122 about a shaft 123 extending about a rotation axis RA. The shaft 123 extends from and is coupled to a motor drive (not shown), such as an electric motor. In one example, the rotor 120 has a star configuration with a plurality of rotor arms 121 disposed radially away from one another by gaps 126 in which are syringe fixture buckets, such as the ones shown in FIGS. 5-6, received. In one example, compartments 128 are formed into the housing in gaps 126, respectively, where such compartments 128 are sized and shaped to receive the fixture buckets. In FIG. 4, the rotor arm 121 has a long arm length LR from the rotation axis RA relative to the length Lf of the sample test syringe 10' of at least 4:1 (centrifuge rotor arm length/syringe barrel length). Using at least a 4:1 ratio can improve the fidelity of the silicone profile away from the matching point. In one example, the centrifuge rotor 120 of the centrifuge system 100 may have sufficient number of compartments to receive six buckets 125, although any number of buckets may be included. Each compartment 128 may be sized and shaped to receive the fixture bucket, shown, for example, in FIGS. 5-6, to retain the syringes 10' in the proper orientation and position.

The operational characteristics of the rotor 120 of centrifuge system 100, that is the speed, whether constant or variable, or other features, are controlled by a system controller 130, shown as dashed to indicate it is housed within the system housing 122. The system controller 130 includes at least one processor 132 in electric communication with and internal memory 134 (e.g., internal flash memory, on-board electrically erasable and programmable read-only memory (EEPROM), etc.) and a power source, such as a voltage source. The system controller 130 may be coupled to a variety of operational sensors 136 that are integrated with the centrifuge and includes control logic operative to perform the operations described herein to control operations of the centrifuge, such as the revolution rate and operational time. The processor 132 includes controls logic operative to perform the operations described herein, including starting and stopping the centrifuge. Note that other control mechanisms may be selected, provided that they control the acceleration and time adequately to effect the simulation described heretofore.

In one example, a centrifuge system includes a body, a rotor rotatable relative to the body about a center axis by a motor, a compartment associated with the rotor, one or more syringes having a film of silicone arranged in the compartment in a predefined orientation where a flange end of the syringe is disposed farther away from the center axis than a needle end of the syringe, and a controller operably coupled to the motor, the controller configured to: activate a centrifugation of the syringe at a predetermined G rate and for a period of a centrifuge run time (tfc), wherein the simulation time is expressed: $tfg/tfc=((r\_C+zL\_F)\omega^2)/g)$, where tfg is a gravity drainage time to be simulated and tfc is a centrifuge run time at speed ω in the centrifuge system with a rotor arm length of rc, a matching point of z, a length of the syringe of LF, and g is an acceleration due to gravity. In one example, the ratio of the rotor arm length to a syringe length is greater than or equal to 4:1. The predetermined G rate is constant or is variable. The product of zLf can be multiplied by a T_fct factor, wherein T_fct factor is a value between 0 and 1. In one example, T_fct factor is 0.5. The system may include a bucket fixture configured to retain the syringe in the predefined orientation, wherein the compartment is configured to receive the bucket fixture. The bucket fixture may include a body defining a plurality of holding cells having a diameter sized to receive a barrel of the syringe and sized to not receive the flange end of the syringe, and a base plate defining a plurality of recesses arranged in coaxial alignment with a corresponding holding cell of the body, each of the recesses having a diameter sized greater than the diameter of the holding cell and sized to receive the flange end of the syringe, and a depth sized to capture a thickness of the flange end of the syringe, the base plate including attachment features for secure attachment to the lower end of the body.

Figure 5:
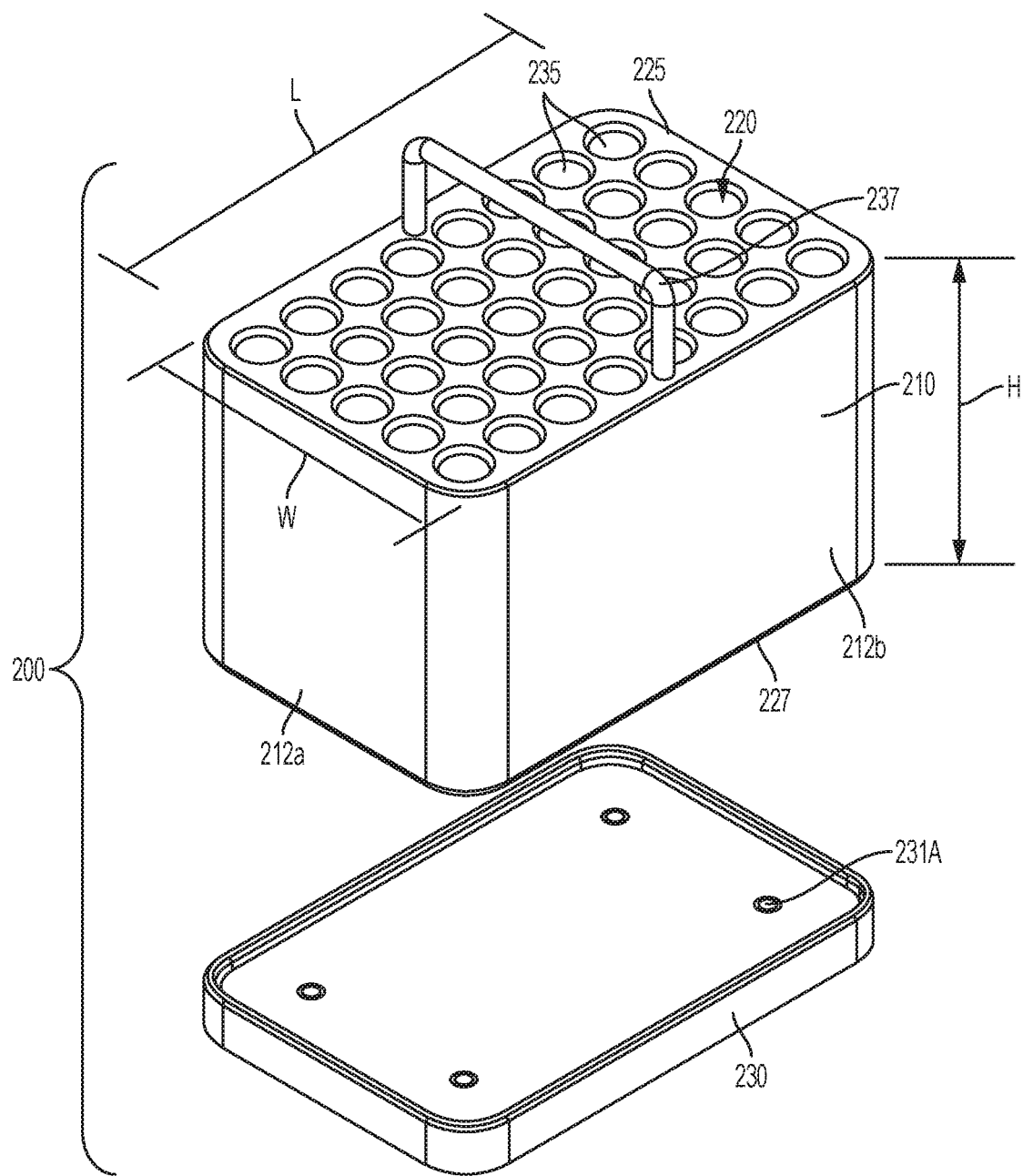
FIG. 5 is a perspective view of an upper end of a fixture bucket to hold a plurality of syringes within the centrifuge system in FIG. 3 during testing, illustrating a body of the fixture bucket in its upright position with a base removed from a lower end of the fixture body.
Figure 6:
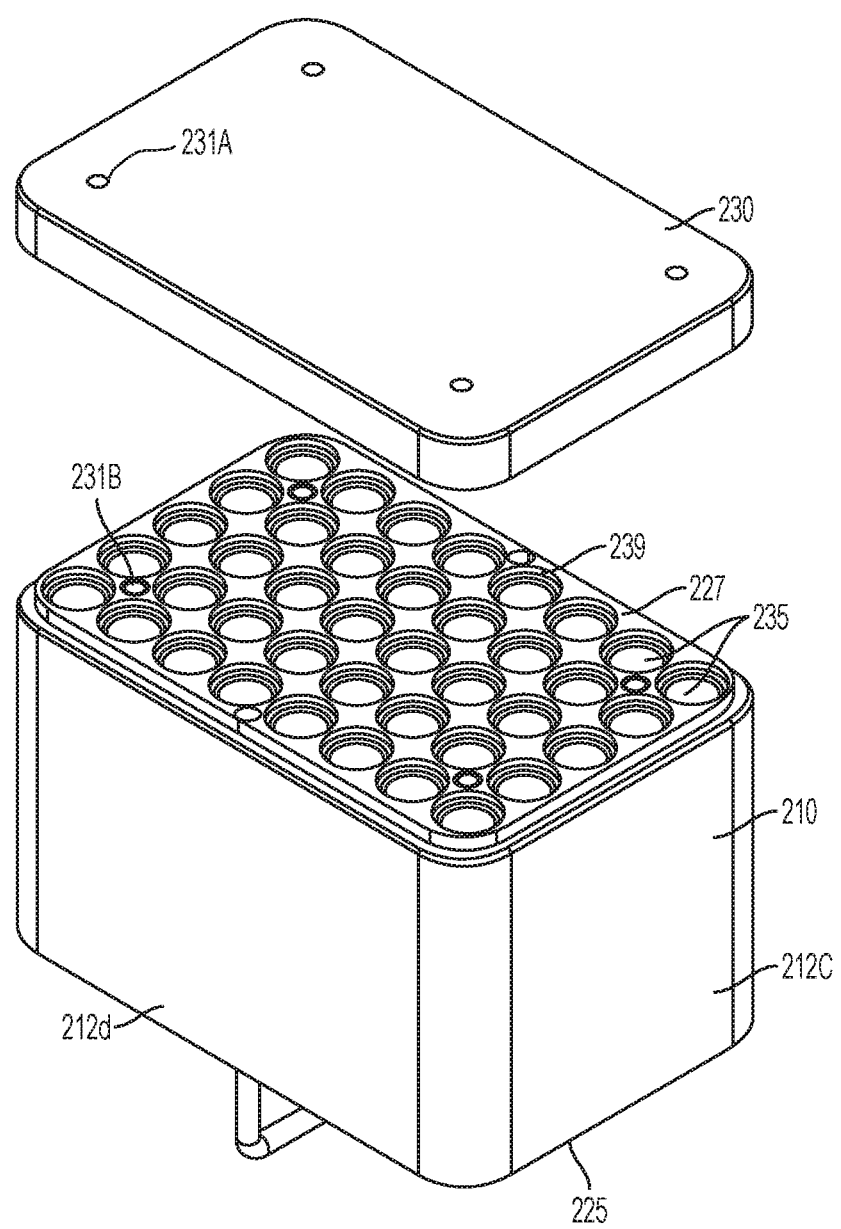
FIG. 6 is a perspective view of a lower end of the fixture bucket in FIG. 5 with the base removed.
Figure 8:
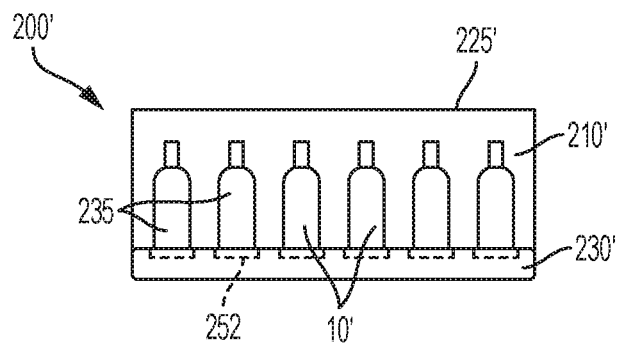
FIG. 8 is a cross-sectional view of the fixture bucket in FIG. 7, taken along a set of linearly aligned holding cells with syringes therein and with the base of FIG. 7 of the fixture bucket attached to its body.

An exemplary embodiment of a fixture bucket assembly 200 is shown in FIGS. 5-6. The fixture assembly 200 includes a body 210 in a cuboidal shape having generally body sides 212*a-d* defining a body length L, a body width W, and a body height H, respectively. The fixture body 210 may be solid or its sides may define a cavity 220. FIG. 5 illustrates in an upper end perspective view of an upper end 225 of the bucket body 210 in its upright position with a removable base 230 removed from a lower end 227. FIG. 6 illustrates in a lower end perspective view the opposite lower end 227 of the bucket body 210 with the base 230 removed. The bucket body 210 may include a plurality of holding cells 235 extending at least partially between the upper end 225 and the lower end 227 of body 210. The holding cells 235 may be in any arrangement, including 5×8 pattern that is shown. The holding cells 235 may be formed by machining bores between the upper end and the lower end or by a casting process. The holding cells may be shaped similarly to a common syringe shape, as shown in FIG. 4 and FIG. 8. That is, as shown, the syringe shape includes an end or a reduced cross-sectional area (or reducing cross-sectional area) that is associated with the needle end of the syringe, an intermediate linear region of a constant cross-sectional area that is associated with syringe barrel, and an enlarged cross-sectional area that is associated with the flange end of the syringe. The lower end 239 of the holding cells 235 in associated with the lower end 227 of the bucket body 210, and may define a conically tapered surface sized to receive the cross-sectional area of the flange end 12 of the syringe. As shown, each of the cells 235 may be sized to receive the syringe barrel but not the flange end, as the flange end is shown projecting radially outward beyond the syringe barrel by a diameter 12*b*. The tapered surface is angled in a manner to accommodate for the thickness of the flange end (shown as thickness 12*a* in FIG. 1), so that the flange does not project beyond the planar surface defined by the lower end 227 of body 210. Base 230 is sized to cover all of the holding cells 235. As shown, the base 230 may couple to the bucket body by mechanical fasteners (not shown) in alignment with respective threaded openings 231A, 231B in the base and the bucket body. As shown, the bucket body 210 includes a handle 237 mounted to the upper end 225. In one example, the handle 237 has a U-shaped body with two attachment ends coupled to the upper end 225 and a portion extending between the two attachment ends in parallel and spaced relationship with the planar surface defined by the upper end 225 of body 210, as shown.

Figure 7:
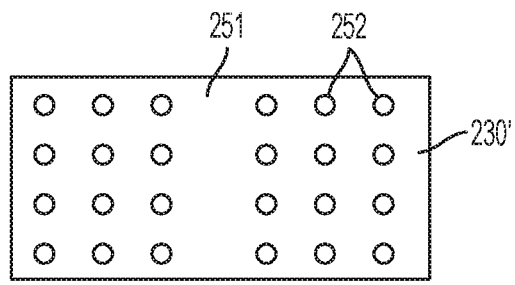
FIG. 7 is an upper axial view of a base plate of another embodiment of a fixture bucket, depicting the location of a plurality of holding cells.
Figure 9:
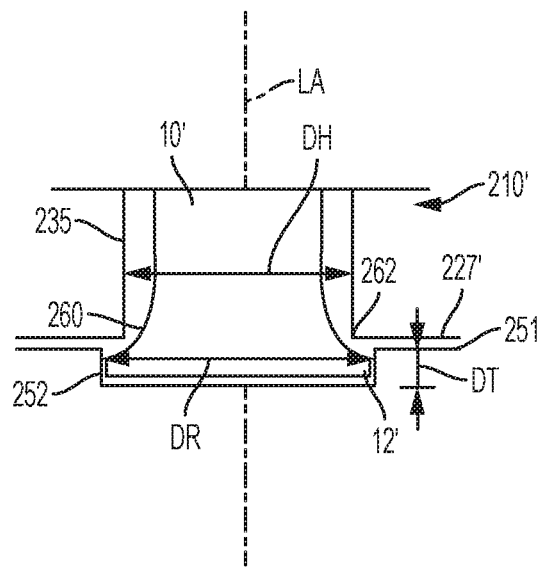
FIG. 9 is a detailed cross-sectional view of the bottom of one of the holding cells with the syringe disposed therein and with the base attached to the fixture bucket.

The syringes are placed within the holding cells 235 with the flange end away from the center of the rotor. The syringe's placement in the fixture bucket is shown in FIG. 4. FIGS. 7-9 illustrate another embodiment of a fixture bucket assembly, now referred to as 200'. In FIG. 7, an upper surface 251 of another example of the base, now referred to as base 230', that faces the lower end 227' of the bucket body, now referred to as bucket body 210', when attached, defines a plurality of recesses 252 arranged in alignment with corresponding holding cells formed in the bucket body of fixture bucket assembly 200'. Attachment features have been omitted from the base 230' for clarity. In FIG. 8, a cross-sectional figure of the interface of the recesses 252 and the end of the holding cell 235 that receives the syringe. The cross-sectional area or diameter of the recess (DR) may be greater than the cross-sectional area or diameter of the cell (DH). The combination of the depth of the recess (DT) and the diameter of the recess (DR) is sized to permit the flange 12' of the syringe 10' to fit snugly therein. To this end, with the base plate 230' removed, the syringe 10' will be inserted in a predetermined orientation within the cell 235 from the lower end 227' such that the needle end 14 of the syringe 10' is in closer proximity to the upper end 225' of the bucket body 210' than to the lower end 227' of the bucket, as shown in FIG. 9. The cross-sectional area or diameter of the syringe flange (diameter 12*b* in FIG. 1) is greater than the cross-sectional area or diameter of the cell (DH) so that the flange projects outward from the lower end 227' of the bucket body 210'. To this end, an under surface 260 of the syringe flange 12' is engageable with the corner edge 262 that defines the intersection of the holding cell 235 with the lower end 227' of the body 210'. After insertion of all of the syringes (a partial number of the cells may be left empty), the base plate 230' may be securely attached to the lower end of the bucket. For example, mechanical fasteners may be used between the lower end of the bucket and the base plate. The base plate 230' may be configured to apply an increased pressure between the syringe flange 12' and the edge 262 for secured retainment of the syringe within the fixture bucket at a fixed location during operation of the centrifuge.

Such as shown in FIG. 4, the fixture bucket 200 or 200' is secured to the rotor arm 121 of the rotor 120 of the centrifuged system 100 such that the syringe flange end 12 or 12' of the syringe is farthest from the rotation axis RA of the centrifuge to allow for drainage towards the flange end. Multiple buckets may be secured to corresponding arms of the system. The centrifuged system 100 is activated a predetermined G-rate (or radial acceleration rate) and for a period of time selected for the intended simulation. The centrifugation is ended after the period of intended simulation time has elapsed. After centrifugation, one or more injection functionality parameters of the syringe is assessed.

Figure 19:
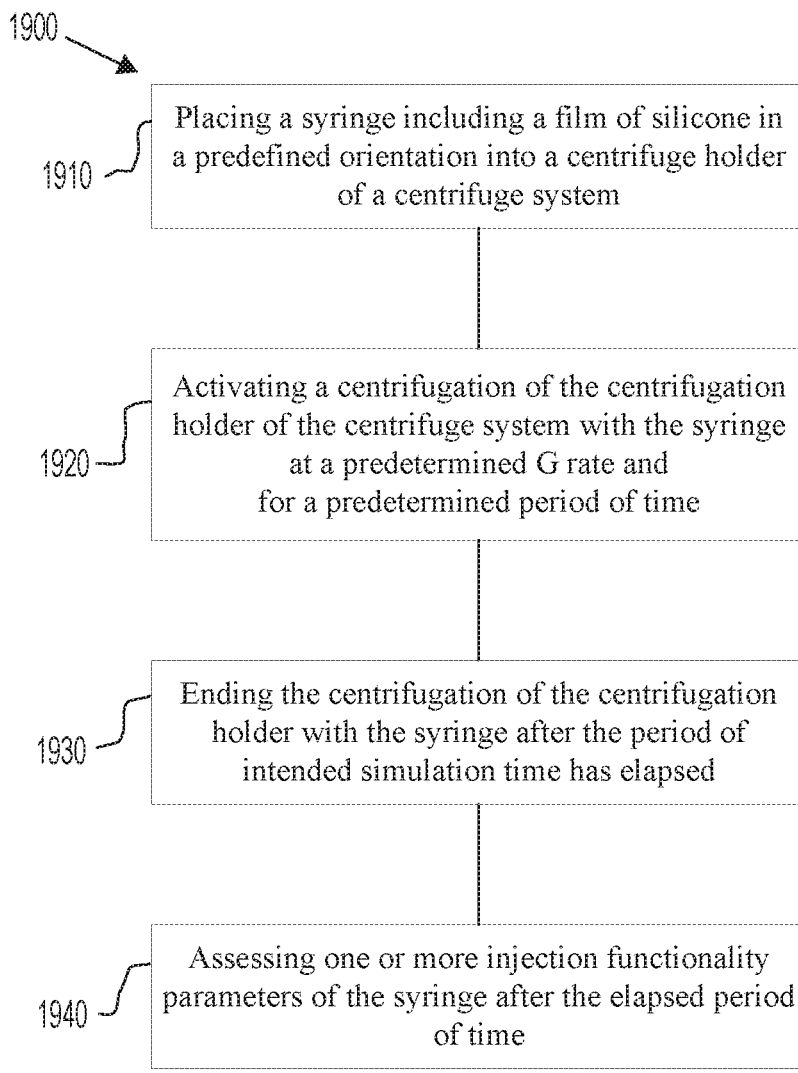
FIG. 19 is flow diagram indicative of an exemplary test method.

One example of a testing method, referred to as 1900, for accelerating silicone drainage rate for an empty pre-filled siliconized syringe is shown in FIG. 19. The method may include one or more of the following steps: (a) Placing a syringe including a film of silicone in an predefined orientation into a centrifuge holder of a centrifuge system (step 1910). One preferred orientation corresponds to the expected storage orientation. For a typical "needle up" storage, this orientation corresponds to an orientation where the needle end is disposed away from acceleration (or in other words, the syringe flange end is farther from the center axis of the centrifuge than the needle end). As described herein, other syringe orientations may be employed. (b) Activating a centrifugation of the centrifugation holder of the centrifuge system with the syringe at a predetermined G rate and for a period of intended simulation time (step 1920). (c) Ending the centrifugation of the centrifugation holder with the syringe after the period of intended simulation time has elapsed (step 1930). (d) Assessing one or more injection functionality parameters of the syringe, such as silicone layer dependent characteristics, after the elapsed period of time (step 1940). In another example, the siliconized syringe is a non-cross-linked siliconized syringe. In another example, the time elapsed is expressed as $$\frac{t_{fg}}{t_{fc}} = \frac{(r_C + zL_F)\omega^2}{g}$$

where $t_{fg}$ is the gravity drainage time to be simulated and $t_{fc}$ is the centrifuge run time at speed $\omega$ in a centrifuge with an arm length of $r_c$, a matching point of z, a syringe length of $L_F$, and g is the acceleration due to gravity. In other examples, said parameters includes any one of break-loose force, glide force, total silicone content, silicone layer profile, self-injection device injection time, or any combination thereof.

The assessment in step 1940 may be accomplished by filling (which optionally can be air for assessing syringe break loose and plunger glide forces) and plungering the syringe, then testing with a suitable fixture and force-displacement test stand to determine break-loose force and glide force. A suitable description can be found in ISO 11040. Silicone content can be accomplished by any relevant analytical method, including gravimetrically weighing empty syringe both pre- and post-solvent extraction to remove the silicone and drying to remove the solvent. Alternatively, the solvent can also be collected and assayed to determine the quantity of silicone extracted. For determining the silicone layer profile, an analytical method to characterize sprayed-on silicone oil layers in empty prefilled syringes may be used, such as, with reference to PDA J Pharm Sci Technol. 2018 May-June; 72(3):278-297. doi: 10.5731/pdajpst.2017.007997. Epub 2018 Jan. 17.

One of the benefits of the method is the provision of accelerated data for clinical trials. Another of the benefits is to enable better and faster data set for drug filing. Results may lead to changes in container enclosure system or lubrication profile. The testing method provides a use of centrifugation to model long term effect of gravity pull.

Figure 10:
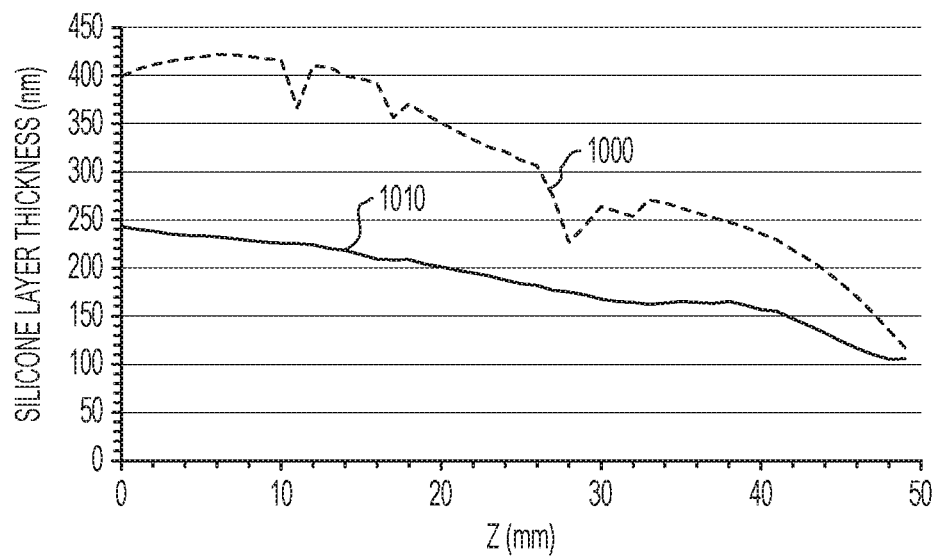
FIG. 10 depicts a plot graph of a film layer profile in nanometers along a barrel length (z) of a syringe sample for Pre and Post Centrifugation (centrifugation for the equivalent of 2 years).

An example test method, such as method 1900, is performed with the centrifuged system 100. An example of the data resulting from applying the method is shown in FIG. to, which shows the pre- and post-silicone layer profiles, the silicone layer thickness in nanometer vs. distance in the z direction in millimeters for equivalent of 2 years, for sample 4. The first curve 1000 is the initial (pre centrifugation) silicone profile and the second curve 1010 is the silicone profile after (post) centrifugation for the equivalent of 2 years. In the test configuration, the position z=0 is at the open end of the syringe where the measurements start, in this case, with the RapID. With RapID, measurements are from about 1 mm inside the flange (the "zero" on the graph in FIG. 10) to 50 mm inside the flange (the 49 mm point on the graph). The needle end is toward the 50 mm here and the flange end toward the zero here. The symbol Ψ represents the silicone layer thickness at the chosen point divided by the radius of the syringe, using this convention as a convenient way to dedimensionalize the above described equations to generalize the model. The syringe barrel is 54.5 mm long but the measurement device (RapID) can only go to the position z=49 mm (at the needle end). The designation of z in the test results is opposite to that used in the model where z=0 in the model represents the end where z=49 mm in the test results. In FIG. 10, the silicone flows in the negative z direction. Since the syringes are stored needle side up (in this example), this means that the direction of the centrifugal force is in the same direction as the gravitational force.

Figure 11:
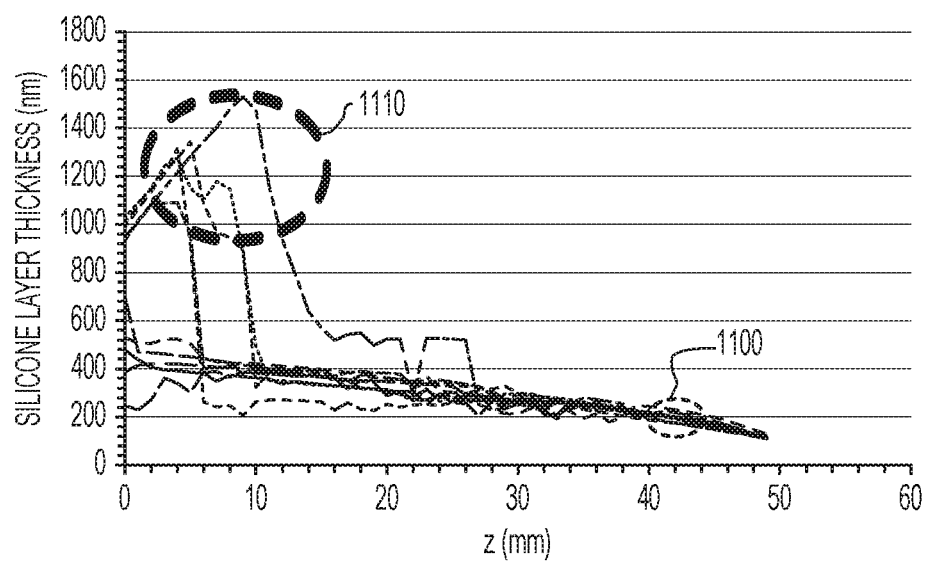
FIG. 11 depicts a plot graph of an initial film layer profile in nanometers along a barrel length (z) of a syringe samples 11-20.
Figure 12:
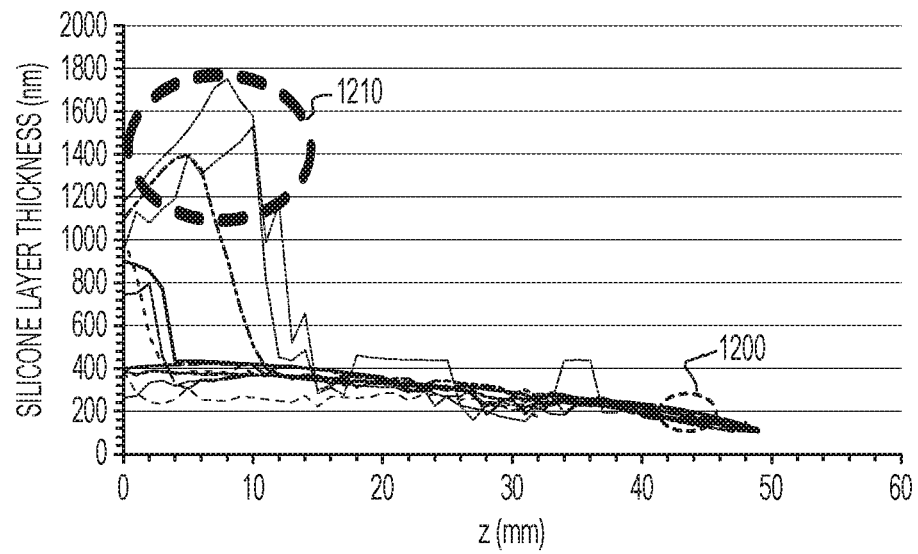
FIG. 12 depicts a plot graph of an initial film layer profile in nanometers along a barrel length (z) of a syringe samples 1-10.

The initial pre silicone layer, the silicone layer thickness in nanometers vs. distance in the z direction in millimeters, for samples 11-20 is shown in FIG. 11 and for samples 1-10 in FIG. 12. Both of these charts show that the samples have low sample to sample variation for larger z values (close to the needle end), at graph region 1100 in FIG. 11 and at graph region 1200 in FIG. 12, respectively, and larger sample to sample variation at z=0 (flange) end, at graph region 1110 in FIG. 11 and at graph region 1210 in FIG. 12, respectively. The initial silicone distribution data was used as input to the model that predicted the final distribution after centrifugation and after an equivalent storage time in normal gravity.

Parameter Specification for the Model

Using the above geometrical information, the centrifugation time equivalent to a gravity falling time of 1 year and 2 years can be found based on the ratio of the centrifugal acceleration to the acceleration due to gravity. Results of the Centrifuge time calculations are shown in Table 2.

TABLE 2

| | T_Fct = 0.0 | T_Fct = 0.5 | T_Fct = 1.0 |
|---|---|---|---|
| Length to syring (rc) | 204.5 mm | 204.5 mm | 204.5 mm |
| Length of Barrel | 49 mm | 49 mm | 49 mm |
| ID of Barrel | 8.65 mm | 8.65 mm | 8.65 mm |
| RPM | 3500 rev/min | 3500 rev/min | 3500 rev/min |
| Simulated time 1 | 2 year | 2 year | 2 year |
| Simulated time 2 | 4 year | 4 year | 4 year |
| Length to syring (rc1) | 0.2045 m | 0.2045 m | 0.2045 m |
| Length of Barrel | 0.049 m | 0.049 m | 0.049 m |
| RPM | 58.33 rev/s | 58.33 rev/s | 58.33 rev/s |
| Omega | 366.52 rad/s | 366.52 rad/s | 366.52 rad/s |
| Representative Length | 0.2045 m | 0.229 m | 0.2535 m |

TABLE 2-continued

|  | T_Fct = 0.0 | T_Fct = 0.5 | T_Fct = 1.0 |
| --- | --- | --- | --- |
| Simulated time 1 year | 63072000 s | 63072000 s | 63072000 s |
| Simulated time 2 years | 126144000 s | 126144000 s | 126144000 s |
| Acceleration | 27471.77 m/s² | 30763.01 m/s² | 34054.25 m/s² |
| G | 9.81 m/s² | 9.81 m/s² | 9.81 m/s² |
| G Equivalents | 2800.38 | 3135.88 | 3471.38 |
| Centrifugation Time Required 1 | 22523 s | 20113 s | 18169 s |
| Centrifugation Time Required 2 | 45045 s | 40226 s | 36338 s |
| Centrifugation Time Required 1 | 6.26 hr | 5.59 hr | 5.05 hr |
| Centrifugation Time Required 2 | 12.51 hr | 11.17 hr | 10.09 hr |

The radius used for the centrifugal acceleration is (rC+T_Fct*Lf). There are three sets of calculations shown in Table 2. The first set assumes that the representative value of z to use for the calculations is z=0 (T_Fct=0.0). The results show that for 1 year a centrifugation time of 6.26 hours should be used and for 2 years it should be 12.51 hours. If the value of T_Fct=0.5 is used as the representative point for the centrifuge acceleration calculations then these times are 5.59 hours and 11.17 hours respectively. Finally if the value of T_Fct=1.0 is used as the representative point for the centrifuge acceleration calculations then these times are 5.07 hours and 10.09 hours respectively.

Results

The results of general centrifugation can be demonstrated using the methods described herein. Results can be determined and characterized using the following categories, as shown in Table 3.

TABLE 3

| z (mm) | 0 to 49 mm in dimensionless form (from 0 to 1 in increments of 1/49) |
| --- | --- |
| Psi (t = 0) | The dimensionless Ψ value at t = 0 from the test sample data |
| Psi Gravity | The predicted Ψ from the model for the simulated time (1 or 2 years depending on the sample) under gravity |
| Psi (CentLow) | The predicted Ψ from the model using the centrifuge where the equivalent centrifugation time is calculated using T_Fct = 0.0 |
| Psi (CentMid) | The predicted Ψ from the model using the centrifuge where the equivalent centrifugation time is calculated using T_Fct = 0.5 |
| Psi (CentHigh) | The predicted Ψ from the model using the centrifuge where the equivalent centrifugation time is calculated using T_Fct = 1.0 |
| Err (CentLow) | The difference between the results in (c) and (d) showing the error between the model prediction for gravity and centrifugation assuming that the equivalent time is calculated using T_Fct = 0.0 |
| Err (CentMid) | The difference between the results in (c) and (e) showing the error between the model prediction for gravity and centrifugation assuming that the equivalent time is calculated using T_Fct = 0.5 |
| Err (CentHigh) | The difference between the results in (c) and (f) showing the error between the model prediction for gravity and centrifugation assuming that the equivalent time is calculated using T_Fct = 1.0 |
| Psi(Test Results) | the final test values for Ψ after centrifugation |
| ErrM (CentLow) | the difference between the results in (j) and (d) showing the difference between the model prediction and test results assuming that the centrifugation equivalent time is based on T_Fct = 0.0 |
| ErrM (CentMid) | the difference between the results in (j) and (e) showing the difference between the model prediction and test results assuming that the centrifugation equivalent time is based on T_Fct = 0.5 |
| ErrM (CentHigh) | the difference between the results in (j) and (f) showing the difference between the model prediction and test results assuming that the centrifugation equivalent time is based on T_Fct = 1.0 |

Figure 13:
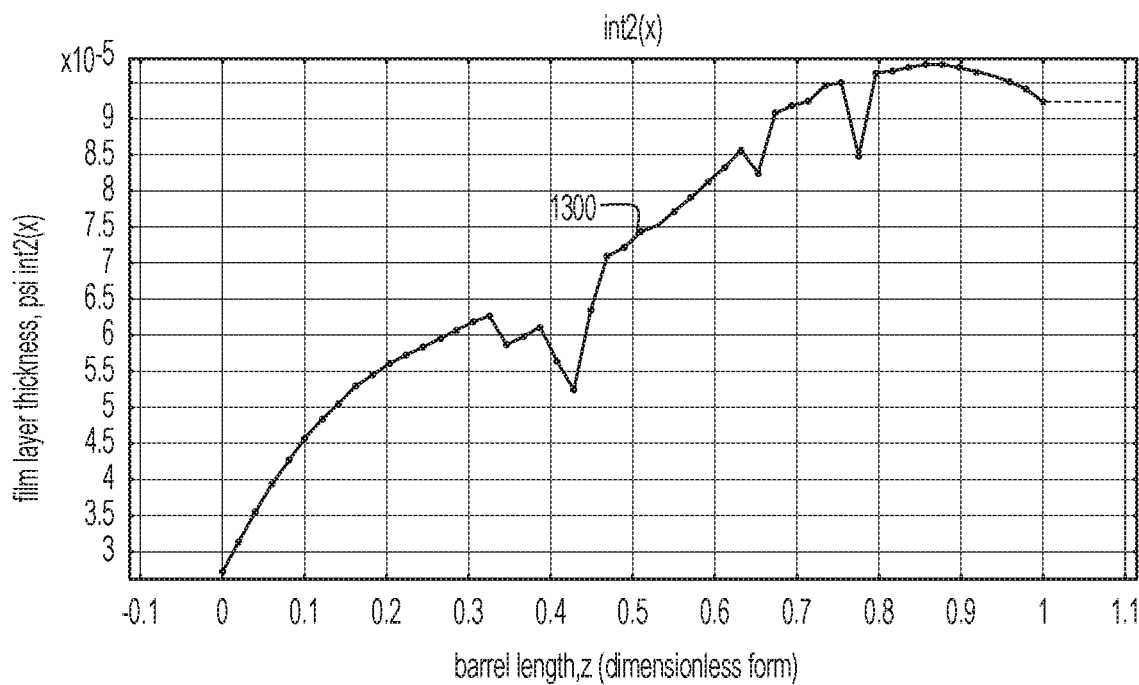
FIG. 13 depicts a plot graph of an initial film layer profile (dimensionless thickness of silicone film layer $\psi$ value) along a barrel length (z in dimensionless form from 0.0 to 1.0) of a syringe sample for Pre Centrifugation (t=0).
Figure 14:
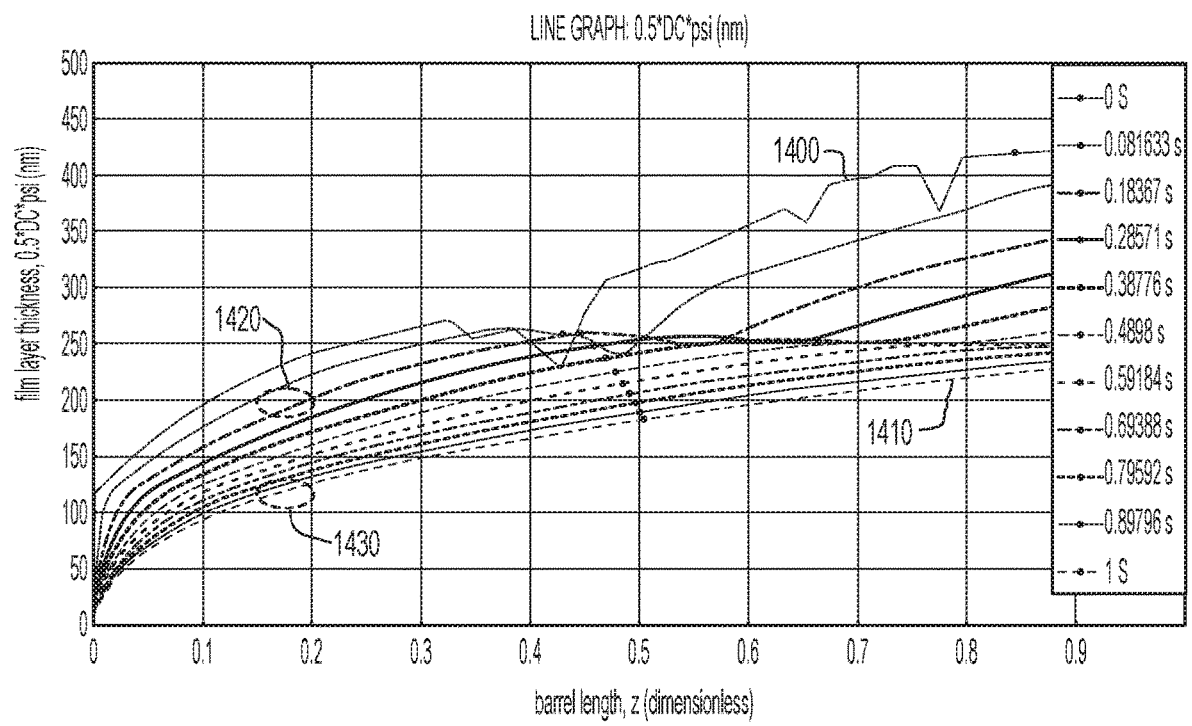
FIG. 14 depicts a plot graph of the model results of the film layer profile (dimensionless thickness of silicone film layer $\psi$ value) along a barrel length (z in dimensionless form from 0.0 to 1.0) of a syringe sample during centrifugation (for equi-spaced times between t=0 and t=1s (the time is scaled so that t=1s is equivalent to 2 years)). Note that the reference dimension for $\Psi$ is the internal syringe radius such that $\Psi$ is the layer thickness at a particular location, z, divided by the internal radius of the syringe barrel.

FIG. 13 shows the initial profile for the silicone layer (Psi, Ψ) along syringe sample 4 at line 1300, with needle end up at 0 and flange end at 1. FIG. 14 shows the model results between this initial profile (Psi) for equi-spaced times between t=0 (at line 1400) and final profile of silicone layer (Psi) for t=1 sec (at line 1410) (the time is scaled so that t=1s is equivalent to 2 years).

The results in FIG. 14 illustrate several features of the model: (a) The model tends to smooth out the silicone layer profile. After 2 years all the kinks in the original profile have disappeared. (b) The impact on the profile is greater at earlier times when the profile is larger than later. This can be seen by the fact that the gap between successive profiles in FIG. 14 is smaller for later time than for earlier times. This was predicted earlier since the wave speed depends on the square of the size of the silicone layer. The dashed ellipses 1420, 1430 in FIG. 14 indicate this difference.

Figure 15:
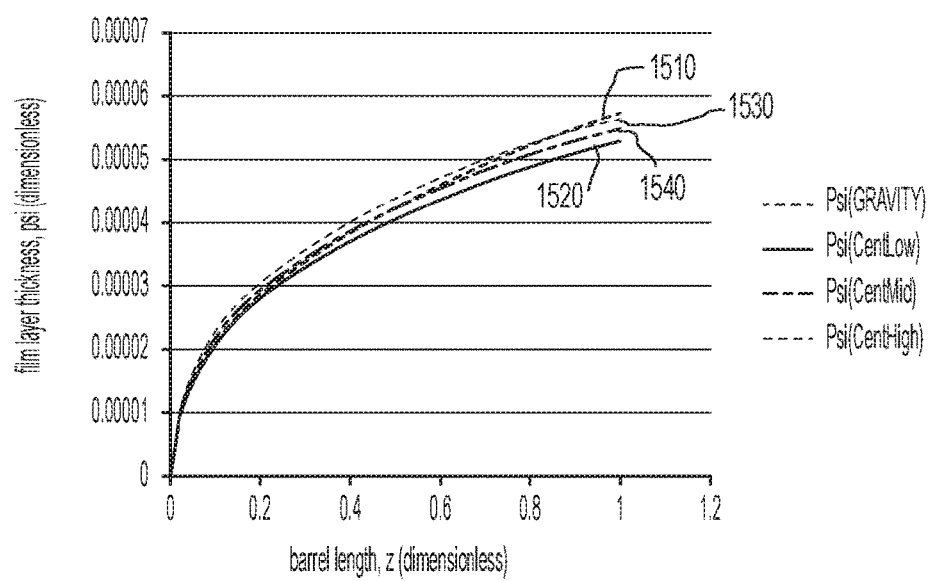
FIG. 15 depicts a plot graph of the predicted values of the film layer profile (dimensionless thickness of silicone film layer $\psi$ value) along a barrel length (z in dimensionless form from 0.0 to 1.0) of the syringe samples, comparing gravity drainage and centrifugation drainage (using the Low (T_Fct=0.0), Mid (T_Fct=0.5), and High (T_Fct=1.0)).

For each sample the following charts can be viewed. In FIG. 15, the predicted values for dimensionless thickness of the silicone layer ψ (Psi) for gravity drainage (at line 1510) and for centrifugal drainage using the Low (T_Fct=0.0) (at line 1520), Mid (T_Fct=0.5) (at line 1540), and High (T_Fct=1.0) (at line 1530) calculation for the equivalent centrifugation time are shown. These charts indicate that the general trends in the gravity drainage case are reproduced by the centrifugation drainage case. The model predictions thus support the use of centrifugation over short time periods to mimic the impact of gravity drainage over long time periods.

Figure 16:
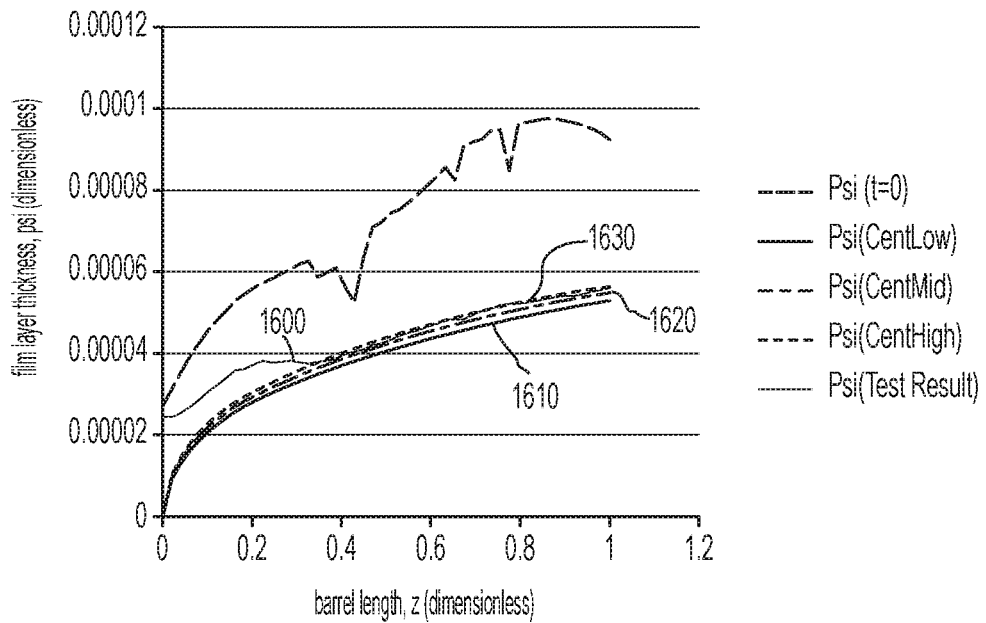
FIG. 16 depicts a plot graph of the film layer profile (dimensionless thickness of silicone film layer $\psi$ value) along a barrel length (z in dimensionless form from 0.0 to 1.0) of a syringe sample, comparing the initial profile (t-o), the model results of centrifugation drainage (using the Low (T_Fct=0.0), Mid (T_Fct=0.5), and High (T_Fct=1.0)), and the test results.

FIG. 16 compares the test results for dimensionless thickness of the silicone layer ψ along the centerline of the syringe at the end of centrifugation (at line 1600) with the model predictions of dimensionless thickness of the silicone layer ψ using the Low (T_Fct=0.0) (at line 1610), Mid (T_Fct=0.5) (at line 1620), and High (T_Fct=1.0) (at line 1630) calculation for the equivalent centrifugation time. This chart shows that the comparison between model and test results is good except for the initial region where there is inaccuracy since the measuring system cannot extend to the end and there is likely to be silicone in this region which will flow into the region that is measured at z=0 and so the test results are expected to be higher here than what the model predicts.

Figure 17:
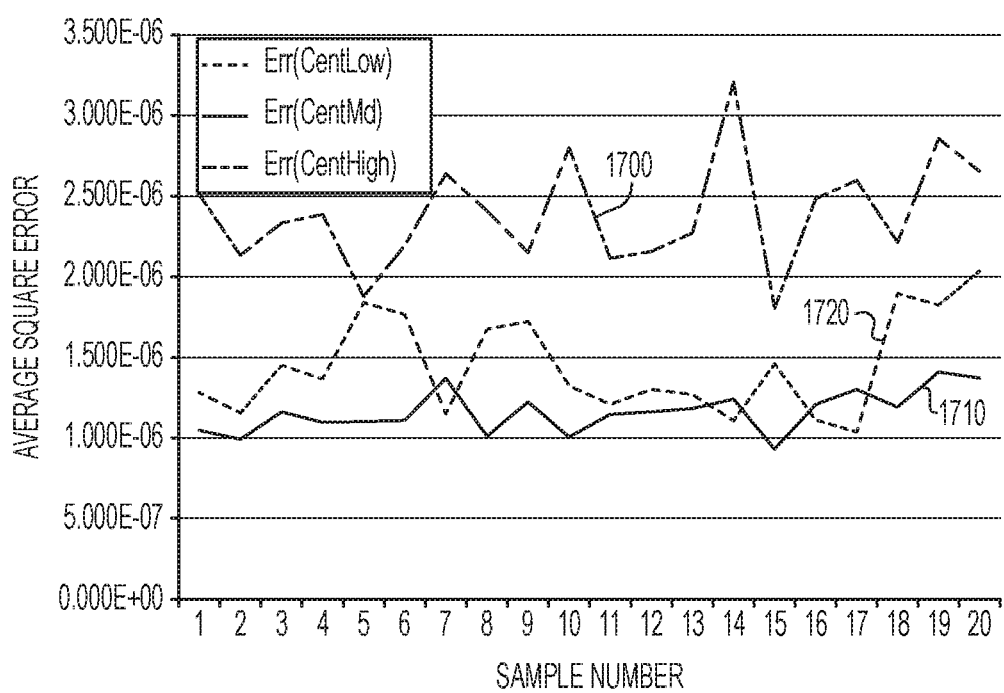
FIG. 17 depicts a plot graph of the average square error between the model results for gravity and for centrifugation of all the samples at the three equivalent times Low (T_Fct=0.0), Mid (T_Fct=0.5), and High (T_Fct=1.0).

The next sections look at summary of the results across all the samples. FIG. 17 shows the average square error between the model results for gravity and for centrifugation at the three equivalent times Low (T_Fct=0.0) (at line 1700), Mid (T_Fct=0.5) (at line 1710), and High (T_Fct=1.0) (at line 1720). This graph shows that of the three choices, using the mid-point of the syringe to calculate the representative centrifugal force (to calculate the equivalent centrifugation time) is one of the preferred choices to match silicone content reduction over time. For other devices or characteristics, other matching points between 0 and 1 may be more desirable for assessing other characteristics and that the matching point selected may also depend on the application.

Figure 18:
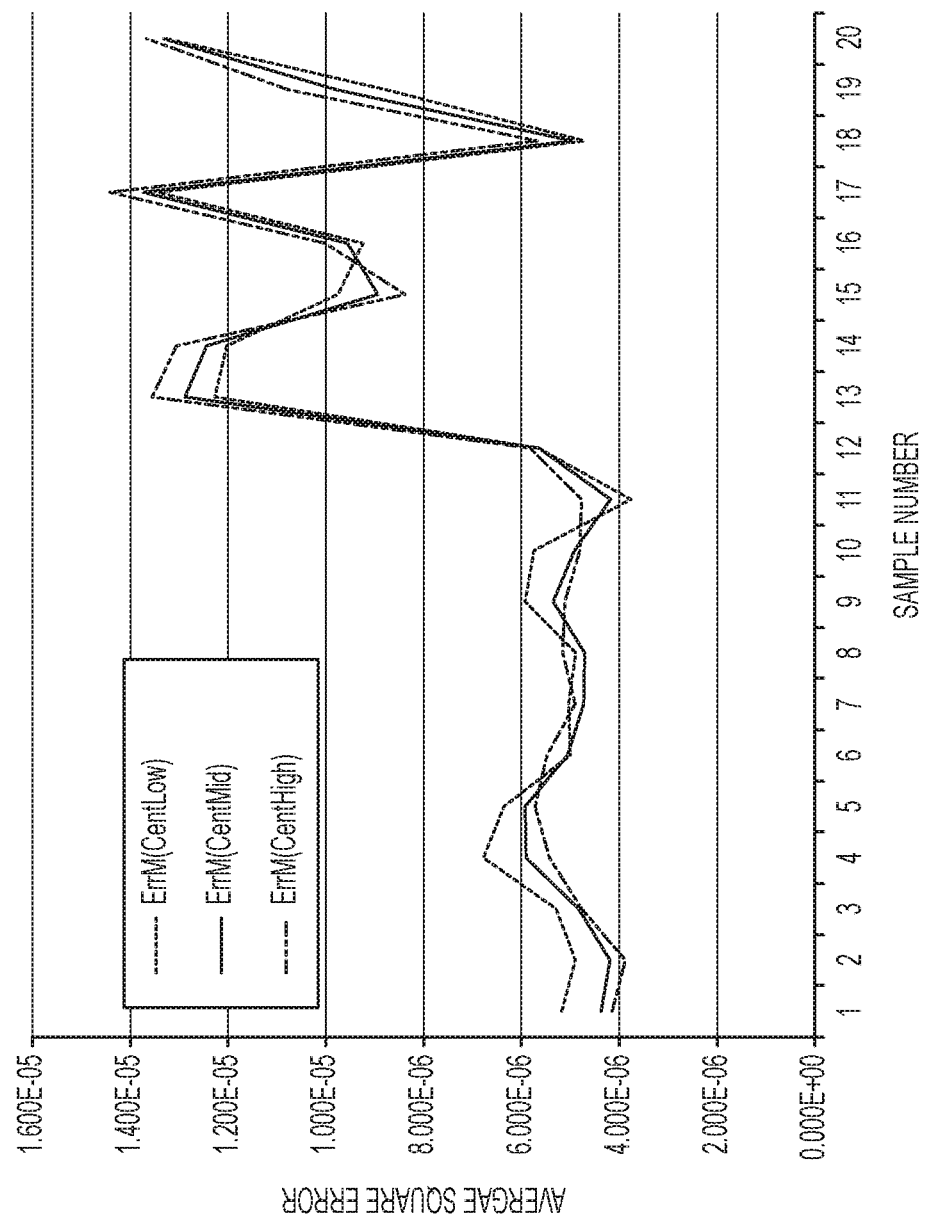
FIG. 18 depicts a plot graph of the average square error between the model results and test results for centrifugation of all the samples at the three equivalent times Low (T_Fct=0.0), Mid (T_Fct=0.5), and High (T_Fct=1.0).

FIG. 18 shows the Average Square Error between the Model Prediction and the Test Results for all 20 samples. The following observations can be made from this graph in FIG. 18. The model error is consistent between the 1-10 sample set (two year simulation) and the 11-20 sample set (1 year simulation). That is, all 1 year samples have around the same average square error and all the 2 year samples have around the same average square error. The model prediction matches the test results significantly better for samples 1-10 at year 2 than for sample 11-20 at year 1. This indicates that as the drainage goes on for longer time the model predictions get better. This is likely due to the fact that at longer times more of the silicone has drained out and the layer thickness is changing less with time. The difference between the average square error for the different T_Fct values (Low, Mid, High) is smaller than the variability between samples and so it cannot be concluded from this data which value of T_Fct is the best value to use to calculate the equivalent centrifugation time. The data in FIG. 18 gives a better indication of this as discussed herein. The agreement between the model prediction and the test results after 2 years is very good. As already discussed the region close to z=0 does not fit well because this region is fed by the silicone layer for z<0 which the measuring device cannot measure.

It is possible to model the drainage of the silicone layer in syringes using a centrifuge to accelerate the drainage and get results that agree reasonably well with experiment especially for longer periods of time. Given also that the model shows that the predicted results using a centrifuge, which has a large enough radius to minimize the effects of acceleration variation along the syringe, are similar to the results obtained under gravity drainage using an equivalent centrifugation time, it can be concluded that accelerated testing of silicone drainage using a centrifuge running for an equivalent drainage time will reproduce drainage under gravity. Further the results show that the best point to use to estimate silicone drainage from the syringe over time comes by matching the centrifugal force at the point that is halfway along the syringe length and that other matching points may be more appropriate for a specific combination of syringe properties of concern (silicone layer thickness, glide force, etc.) and a specific application (i.e. a manual prefilled syringe, an autoinjector, or a bolus injector).

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations. Furthermore, the advantages described above are not necessarily the only advantages, and it is not necessarily expected that all of the described advantages will be achieved with every embodiment.

Various aspects are described in this disclosure, which include, but are not limited to, the following aspects:

1. A testing method for accelerating silicone drainage rate for a siliconized syringe, comprising: placing a syringe including a film of silicone in a predefined orientation into a centrifuge holder of a centrifuge system, the syringe including a needle end and an opposite, flange end, the predefined orientation of the syringe including the flange end being disposed farther away from a center axis of the centrifuge system than the needle end or the needle end being disposed farther away from the center axis of the centrifuge system than the flange end; activating a centrifugation of the centrifugation holder of the centrifuge system with the syringe at a predetermined G-rate and for a predetermined period of a time; ending the centrifugation of the centrifugation holder with the syringe after the period time has elapsed; and assessing one or more injection functionality parameters of the syringe after the elapsed period of time.

2. The testing method of aspect 1, wherein the film of the syringe includes a non-cross-linked silicone.

3. The testing method of any one of the preceding aspects, wherein the time elapsed is expressed as (t)=[(intended simulation time) (acceleration due to gravity)]÷[(square of centrifuge revolution rate)(Distance from center of rotor hub to matching point on the syringe barrel)].

4. The testing method of any one of the preceding aspects, wherein a ratio of a length of a rotor arm of the centrifuge system to a length of a barrel of the syringe is greater than or equal to 4:1.

5. The testing method of any one of the preceding aspects, wherein one of the parameters includes a break-loose force.

6. The testing method of any one of the preceding aspects, wherein one of the parameters includes a glide force.

7. The testing method of any one of the preceding aspects, wherein one of the parameters includes a silicone content.

8. The testing method of any one of the preceding aspects, wherein one of the parameters includes a silicone layer profile.

9. The testing method of any one of the preceding aspects, wherein one of the parameters includes an injection time of said syringe.

10. The testing method of any one of the preceding aspects, wherein the predetermined G-rate is constant.

11. The testing method of any one of the preceding aspects, wherein the predetermined G-rate is variable.

12. A testing method for accelerating silicone drainage rate for a siliconized syringe, including: placing a syringe including a film of silicone in a predefined orientation into a centrifuge holder of a centrifuge system, the syringe including a needle end and an opposite, flange end, the predefined orientation of the syringe including the flange end being disposed farther away from a center axis of the centrifuge system than the needle end or the needle end being disposed farther away from the center axis of the centrifuge system than the flange end; activating a centrifugation of the centrifugation holder of the centrifuge system with the syringe at a predetermined G-rate and for a predetermined period of a time (tfc), wherein the period of time (tfc) is expressed:

$$\frac{t_{fg}}{t_{fc}} = \frac{(r_C + zL_F)\omega^2}{g}$$

where $t_{fg}$ is a gravity drainage time to be simulated and $t_{fc}$ is the centrifuge run time at speed $\omega$ in the centrifuge system with a rotor arm length of $r_c$, a matching point of z, a length of the syringe of $L_F$, and g is an acceleration due to gravity; and ending the centrifugation of the centrifugation holder with the syringe after the period time has elapsed 13. The testing method of aspect 12, wherein a ratio of a length of a rotor arm of the centrifuge system to a length of a barrel of the syringe is greater than or equal to 4:1.

14. The testing method of any one of aspects 12-13, wherein the predetermined G-rate is constant.

15. The testing method of any one of aspects 12-13, wherein the predetermined G-rate is variable 16. The testing method of any one of aspects 12-15, further including assessing one or more injection functionality parameters of the syringe after the elapsed period of time.

17. The testing method of aspect 16, wherein one of the parameters includes at least one of a break-loose force, a glide force, a silicone content, and a silicone layer profile.

18. The testing method of aspect 16, wherein one of the parameters includes an injection time of the syringe, which may be a self-injection syringe device, also referred to as an autoinjector.

19. A syringe testing apparatus for a centrifuge system, the syringe having a barrel with a barrel diameter and a flanged end diameter greater than the barrel diameter, the apparatus including: a body defining a plurality of cells extending between an upper end and a lower end of the body, each of the cells having a diameter sized to receive a barrel of the syringe but not a flange of the syringe; and a base plate defining a plurality of recesses, each of the recesses arranged in coaxial alignment with a corresponding cell of the body, each of the recesses having a diameter sized greater than the diameter of the cell, and a depth sized to capture a thickness of the flange of the syringe, the base plate including attachment features for secure attachment to the lower end of the body.

20. The syringe testing apparatus of aspect 19, wherein each of the holding cells has a syringe shape configuration.

What is claimed:

1. A testing method for accelerating silicone drainage rate for a siliconized syringe, comprising:
    (a) placing a syringe including a film of silicone in a predefined orientation into a centrifugation holder of a centrifuge system, the syringe including a needle end and an opposite, flange end, the predefined orientation of said syringe including the flange end being disposed farther away from a center axis of the centrifuge system than the needle end or the needle end being disposed farther away from said center axis of the centrifuge system than the flange end;
    (b) activating a centrifugation of the centrifugation holder of the centrifuge system with the syringe at a predetermined G-rate and for a predetermined period of a time;
    (c) ending the centrifugation of the centrifugation holder with the syringe after the predetermined period of time has elapsed; and
    (d) assessing one or more injection functionality parameters of the syringe after the elapsed predetermined period of time.

2. The testing method of claim 1, wherein the film of the syringe comprises a non-cross-linked silicone.

3. The testing method of claim 1, wherein the predetermined period of time is expressed as (t)=(an intended simulation time of gravity drainage) (an acceleration due to gravity)÷((square of a centrifuge revolution rate)(a distance from the center axis of a rotor hub of the centrifuge system to a matching point on a barrel of the syringe)).

4. The testing method of claim 1, wherein a ratio of a length of a rotor arm of the centrifuge system to a length of the barrel of the syringe is greater than or equal to 4:1.

5. The testing method of claim 1, wherein one of said parameters includes a break-loose force.

6. The testing method of claim 1, wherein one of said parameters includes a glide force.

7. The testing method of claim 1, wherein one of said parameters includes a silicone content.

8. The testing method of claim 1, wherein one of said parameters includes a silicone layer profile.

9. The testing method of claim 1, wherein one of said parameters includes an injection time of said syringe.

10. The testing method of claim 1, wherein said predetermined G-rate is constant.

11. The testing method of claim 1, wherein said predetermined G-rate is variable.

12. A testing method for accelerating silicone drainage rate for a siliconized syringe, comprising:
    (a) placing a syringe including a film of silicone in a predefined orientation into a centrifugation holder of a centrifuge system, the syringe including a needle end and an opposite, flange end, the predefined orientation of said syringe including the flange end being disposed farther away from a center axis of the centrifuge system than the needle end or the needle end being disposed farther away from said center axis of the centrifuge system than the flange end;
    (b) activating a centrifugation of the centrifugation holder of the centrifuge system with the syringe at a predetermined G-rate and for a predetermined period of a time (tfc), wherein the predetermined period of time (tfc) is expressed:

$$\frac{t_{fg}}{t_{fc}} = \frac{(r_C + zL_F)\omega^2}{g}$$

where $t_{fg}$ is a gravity drainage time to be simulated and $t_{fc}$ is a centrifuge run time at a speed $\omega$ in the centrifuge system with a rotor arm length of $r_c$, a matching point of z, a length of the syringe of $L_F$, and g is an acceleration due to gravity; and
    (c) ending the centrifugation of the centrifugation holder with the syringe after the predetermined period of time has elapsed.

13. The testing method of claim 11, wherein a ratio of a length of a rotor arm of the centrifuge system to a length of a barrel of the syringe is greater than or equal to 4:1.

14. The testing method of claim 12, wherein said predetermined G-rate is constant.

15. The testing method of claim 12, wherein said predetermined G-rate is variable.

16. The testing method of claim 13, further comprising assessing one or more injection functionality parameters of the syringe after the elapsed predetermined period of time.

17. The testing method of claim 16, wherein one of said parameters includes at least one of a break-loose force, a glide force, a silicone content, and a silicone layer profile.

18. The testing method of claim 16, wherein one of said parameters includes an injection time.

* * * * *

UNITED STATES PATENT AND TRADEMARK OFFICE
CERTIFICATE OF CORRECTION

PATENT NO. : 10,627,377 B2
APPLICATION NO. : 16/495774
DATED : April 21, 2020
INVENTOR(S) : Bernard Michael McGarvey and Brian Frank Lewis Page 1 of 1

It is certified that error appears in the above-identified patent and that said Letters Patent is hereby corrected as shown below:

In the Claims

In Column 25, Line 1, In Claim 13, delete "claim 11," and insert -- claim 12, --, therefor.

In Column 25, Line 8, In Claim 16, delete "claim 13," and insert -- claim 12, --, therefor.

Signed and Sealed this
Twenty-third Day of June, 2020

Andrei Iancu
*Director of the United States Patent and Trademark Office*